US008541023B2

(12) United States Patent
O'Hagan

(10) Patent No.: US 8,541,023 B2
(45) Date of Patent: Sep. 24, 2013

(54) IMMUNOGENIC COMPOSITIONS CONTAINING PHOSPHOLIPID

(75) Inventor: Derek O'Hagan, Winchester, MA (US)

(73) Assignee: Novartis Vaccines and Diagnostics, Inc., Emeryville, CA (US)

(*) Notice: Subject to any disclaimer, the term of this patent is extended or adjusted under 35 U.S.C. 154(b) by 0 days.

(21) Appl. No.: 13/270,107

(22) Filed: Oct. 10, 2011

(65) Prior Publication Data

US 2012/0114692 A1  May 10, 2012

Related U.S. Application Data

(62) Division of application No. 10/748,117, filed on Dec. 29, 2003, now Pat. No. 8,034,378.

(60) Provisional application No. 60/436,919, filed on Dec. 27, 2002, provisional application No. 60/513,075, filed on Oct. 21, 2003.

(51) Int. Cl.
*A61K 39/00* (2006.01)
*A61K 39/38* (2006.01)
*A61K 38/00* (2006.01)
*A61K 39/02* (2006.01)
*A61K 45/00* (2006.01)
*A61K 47/00* (2006.01)
*A61K 9/48* (2006.01)
*A61K 9/14* (2006.01)
*A61K 9/16* (2006.01)

(52) U.S. Cl.
USPC .......... 424/455; 424/184.1; 424/234.1; 424/278.1; 424/489; 424/486; 424/450; 424/451; 424/490

(58) Field of Classification Search
None
See application file for complete search history.

(56) References Cited

U.S. PATENT DOCUMENTS

| | | |
|---|---|---|
| 5,603,960 A | 2/1997 | O'Hagan et al. |
| 6,086,901 A * | 7/2000 | O'Hagan et al. ............ 424/283.1 |
| 6,290,973 B1 | 9/2001 | Hawkins et al. |
| 6,303,347 B1 | 10/2001 | Johnson et al. |
| 6,306,405 B1 * | 10/2001 | O'Hagan et al. ............ 424/278.1 |
| 6,355,257 B1 | 3/2002 | Johnson et al. |
| 6,372,227 B1 | 4/2002 | Garcon et al. |
| 6,451,325 B1 | 9/2002 | Van Nest et al. |
| 6,458,370 B1 | 10/2002 | O'Hagan et al. |
| 6,465,633 B1 | 10/2002 | Skeiky |
| 6,534,064 B1 | 3/2003 | O'Hagan et al. |
| 6,764,840 B2 * | 7/2004 | Johnson et al. ................ 435/101 |
| 6,824,793 B1 * | 11/2004 | O'Hagan et al. ............ 424/491 |
| 6,855,492 B2 * | 2/2005 | O'Hagan et al. ................ 435/4 |
| 6,861,410 B1 | 3/2005 | Ott et al. |
| 6,884,435 B1 | 4/2005 | O'Hagan et al. |
| 7,063,967 B2 * | 6/2006 | Johnson et al. ................ 435/101 |
| 7,090,853 B2 | 8/2006 | Kapp et al. |
| 7,357,936 B1 * | 4/2008 | Garcon ...................... 424/278.1 |
| 7,393,630 B2 * | 7/2008 | O'Hagan et al. .................. 435/5 |
| 7,541,020 B2 * | 6/2009 | Johnson et al. .............. 424/1.73 |
| 7,550,145 B2 * | 6/2009 | O'Hagan et al. ............ 424/184.1 |
| 7,604,802 B2 | 10/2009 | O'Hagan et al. |
| 7,641,911 B2 * | 1/2010 | Ott et al. ..................... 424/283.1 |
| 7,731,967 B2 * | 6/2010 | O'Hagan et al. ............ 424/184.1 |
| 7,785,625 B2 * | 8/2010 | Kim et al. ...................... 424/468 |
| 7,947,309 B2 * | 5/2011 | O'Hagan et al. .............. 424/491 |
| 8,021,834 B2 * | 9/2011 | O'Hagan et al. .................. 435/5 |
| 8,034,378 B2 * | 10/2011 | O'Hagan ...................... 424/455 |
| 8,206,749 B1 * | 6/2012 | O'Hagan et al. .............. 424/501 |
| 8,309,139 B2 * | 11/2012 | O'Hagan et al. .............. 424/502 |
| 2002/0002272 A1 | 1/2002 | Houghton et al. |
| 2002/0025329 A1 | 2/2002 | O'Hagan et al. |
| 2002/0136776 A1 | 9/2002 | Fang et al. |
| 2002/0183251 A1 | 12/2002 | Xu et al. |
| 2003/0138453 A1 | 7/2003 | O'Hagan et al. |
| 2003/0170273 A1 | 9/2003 | O'Hagan et al. |
| 2004/0191270 A1 | 9/2004 | Drane et al. |
| 2004/0202669 A1 | 10/2004 | O'Hagan |
| 2005/0118275 A1 | 6/2005 | O'Hagan |
| 2005/0123599 A1 * | 6/2005 | Ott et al. ........................ 424/450 |
| 2005/0169979 A1 | 8/2005 | Michaeli et al. |
| 2005/0245464 A1 | 11/2005 | Yedgar |

(Continued)

FOREIGN PATENT DOCUMENTS

WO  92/00081 A1  1/1992
WO  98/33487  8/1998

(Continued)

OTHER PUBLICATIONS

Andrianov et al, Advanced Drug Delivery Reviews 34 (1998) 155-170.*

(Continued)

*Primary Examiner* — Nita M Minnifield
(74) *Attorney, Agent, or Firm* — Helen Lee; David Bonham

(57) ABSTRACT

Immunogenic compositions containing phospholipid adjuvants, including microparticle and emulsion compositions. According to one aspect of the invention, an immunogenic microparticle composition is provided comprising: water; a polymer microparticle; an antigen adsorbed to the microparticle; and a phospholipid compound, e.g., a synthetic phospholipid compound comprising: (i) one or more phosphoryl groups independently selected from a phosphato group and a phosphodiester group; (ii) a plurality of linear alkane groups. According to another aspect of the invention an immunogenic emulsion composition is provided that comprises: water; a metabolizable oil; an emulsifying agent; an antigen; and a phospholipid compound, e.g., a synthetic phospholipid compound like that above. The emulsion composition is an oil-in-water emulsion having oil and aqueous phases, in which the oil phase is in the form of oil droplets, substantially all of which are less than 1 micron in diameter.

45 Claims, No Drawings

(56) References Cited

U.S. PATENT DOCUMENTS

| | | |
|---|---|---|
| 2007/0077253 A1 | 4/2007 | Haynie |
| 2009/0139636 A1 | 6/2009 | Bauer et al. |
| 2010/0003280 A1 | 1/2010 | O'Hagan et al. |
| 2010/0047271 A1 | 2/2010 | Drane et al. |
| 2010/0150994 A1 | 6/2010 | Kotyla |
| 2010/0173854 A1 | 7/2010 | Dominowski et al. |

FOREIGN PATENT DOCUMENTS

| | | |
|---|---|---|
| WO | 00/06123 | 2/2000 |
| WO | 00/50006 | 8/2000 |
| WO | 00/56282 | 9/2000 |
| WO | 01/36599 A1 | 5/2001 |
| WO | 01/81609 A2 | 11/2001 |
| WO | 02/03961 A1 | 1/2002 |
| WO | 02/26209 A2 | 4/2002 |
| WO | 02/26212 A2 | 4/2002 |
| WO | 03/028661 A2 | 4/2003 |
| WO | 03/070909 A2 | 8/2003 |

OTHER PUBLICATIONS

Jeffery et al, Pharmaceutical Research, (Mar. 1993) vol. 10, No. 3, pp. ISSN: 0724-8741 abstract only.*
O'Hagan et al, Vaccine 20 (2002) 3389-3398.*
Singh et al, Vaccine, 1998, 16/19:1822-1827.*
M.Briones et al., "The Preparation, Characterization, and Evaluation of Cationic Microparticles for DNA Vaccine Therapy," Pharmaceutical Research, vol. 18, No. 5, 2001, pp. 709-712.
J. Kazzaz et al., "Novel Anionic Microparticles Are a Potent Adjuvant for the Induction of Cytotoxic T Lymphocytes Against Recombinant p55 Gag from HIV-1," Journal of Controlled Release, vol. 67, 2000, pp. 347-356.
K.S. Denis-Mize et al., "Plasmid DNA Adsorbed onto Cationic Microparticles Mediates Target Gene Expression and Antigen Presentation by Dendritic Cells," GeneTherapy, vol. 7, 2000, pp. 2105-2112.
Manmohan Singh et al., "Cationic Microparticles Are an Effective Delivery System for Immune Stimulatory CpG DNA," Pharmaceutical Research, vol. 18, No. 10, Oct. 2001, pp. 1476-1479.
Manmohan Singh et al., "Cationic Microparticles: A Potent Delivery System for DNA Vaccines," Proceedings of the National Academy of Science USA, vol. 97, No. 2, Jan 18, 2000, pp. 811-816.
Manmohan Singh et al., "Mucosal Immunization with HIV-1 Gag DNA on Cationic Microparticles Prolongs Gene Expression and Enhances Local and Systemic Immunity," Vaccine, vol. 20, 2002, pp. 594-602.
Derek O'Hagan et al., "Induction of Potent Immune Responses by Cationic Microparticles with Adsorbed Human Immunodeficiency Virus DNA Vaccines," Journal of Virology, vol. 75, No. 19, Oct. 2001, pp. 9037-9043.
Hawkins, Lynn D. et al., "A Novel Class of Endotoxin Receptor Agonists with Simplified Structure, Toll-Like Receptor 4-Dependent Immunostimulatory Action, and Adjuvant Activity," Journal of Pharmacology and Experimental Therapeutics, vol. 300, No. 2, 2002, pp. 655-661.
Johnson, David A., "Synthesis and Biological Evaluation of a New Class of Vaccine Adjuvants: Aminoalkyl Glucosaminide 4-Phosphates (AGPs)," Bioorganic & Medicinal Chemistry Letters, vol. 9, 1999, pp. 2273-2278.
Haining et al., J. Immunology, 2004, 173:2578-2585.
Fortin et al., Histochemistry and Cytochemistry, 2001, 49/11:1407-1420.
O'Hagan et al., Advanced Drug Delivery Reviews, 1998, 32:225-246.
O'Hagan et al., Molecular Medicine Today, Feb. 1997, pp. 69-75.
Giuliani et al., PNAS, 2006, 103/29:10834-10839.
Gupta et al, Vaccine, 1995 13/14:1263-1276.
O'Hagan et al, Vaccine, 2000, 18:1793-1801.
Dhiman et al, FEMS Immunology and Medical Microbiology, 1998, 21:19-28.
O'Hagan et al, Biomolecular Engineering, 2001, 18:69-85.
Gregoriadis, Immunology Today, 1990, 11/3:89-97.
O'Hagan, In: New Generation Vaccines, ed. Levine et al, 2004, pp. 259-270.
Muderhwa et al., J. Pharmaceutical Sciences, 1999, 88/12:1332-1339.
Vordermeier et al., Vaccine, 1995, 13/16:1576-1582.
Haining et al, Blood, Nov. 16, 2002, 100/11:Abstract No. 2648 abstract only.
Muttilainen et al., Microbial Pathogenesis, 1995, 18:423-436.
Cox et al., Vaccine, 1997, 15/3:248-256.
Delgado et al., Vaccine, 1999, 17:2927-2938.
O'Hagan et al., Vaccine, 1989, 7/5:421-424 abstract only.
Zauner et al., Biol. Chem. 2001, 382:581-595.
Kersten et al., Expert Rev. Vaccines, 2004, 3/4:453-462.
Alving, Vaccine, 2002, 20:S56-S64.
Kwissa et al., Expert Rev. Vaccines, 2007, 6/5:673-684.
Singh et al., Expert Rev. Vaccines, 2007, 6/5:797-808.

* cited by examiner

IMMUNOGENIC COMPOSITIONS CONTAINING PHOSPHOLIPID

STATEMENT OF RELATED APPLICATIONS

This application is a divisional of U.S. patent application Ser. No. 10/748,117, filed Dec. 29, 2003, issuing as U.S. Pat. No. 8,034,378, which is incorporated in its entirety herein by reference and which claims the benefit of priority to provisional patent application No. 60/436,919 filed Dec. 27, 2002 and to U.S. provisional patent application No. 60/513,075 filed Oct. 21, 2003, each of which is incorporated in its entirety herein by reference.

FIELD OF THE INVENTION

The present invention relates generally to pharmaceutical compositions. In particular, the invention relates to immunogenic compositions comprising phospholipid adjuvants.

BACKGROUND

The emergence of subunit vaccines created by recombinant DNA technology has intensified the need for safe and effective adjuvant-containing compositions. Subunit vaccines, while offering significant advantages over traditional live and killed vaccines in terms of safety and cost of production, generally present isolated polypeptides or mixtures of isolated polypeptides to the immune system, which have limited immunogenicity as compared to, for example, whole viruses, bacteria and so forth. As a result, these vaccines generally benefit from adjuvants with significant immunostimulatory capabilities, which help them to reach their full potential in treating disease.

Traditional live vaccines, on the other hand, commonly do not require adjuvants. Moreover, killed vaccines are generally more immunogenic than subunit vaccines and commonly do not require adjuvants. Nonetheless, these vaccines, like subunit vaccines, can also benefit from adjuvants having significant immunostimulatory capabilities.

SUMMARY OF THE INVENTION

The present invention relates to immunogenic compositions comprising adjuvants having significant immunostimulatory capabilities, and in particular, compositions comprising phospholipid adjuvants.

According to a first aspect of the invention, an immunogenic composition is provided which comprises: (a) a pharmaceutically acceptable excipient; (b) a polymer microparticle comprising a biodegradable polymer, for example, a polymer selected from a poly(α-hydroxy acid), a polyhydroxy butyric acid, a polycaprolactone, a polyorthoester, a polyanhydride, and a polycyanoacrylate; (c) an antigen adsorbed to the microparticle; and (d) a phospholipid compound, for example, a synthetic phospholipid compound comprising: (i) one or more phosphoryl groups (wherein a phosphoryl group is represented by the radical =P=O), typically independently selected from a phosphato group,

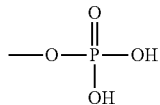

and a phosphodiester group

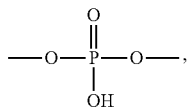

and (ii) a plurality (typically, three to ten, more typically four to eight, even more typically six) of linear alkane groups,

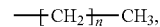

in which n is independently an integer ranging from 6 to 20, i.e., 6, 7, 8, 9, 10, 11, 12, 13, 14, 15, 16, 17, 18, 19 or 20, including pharmaceutically acceptable salts where appropriate.

In many embodiments, the microparticles are formed from a poly(α-hydroxy acid), such as a poly(lactide) ("PLA"), a copolymer of lactide and glycolide, such as a poly(D,L-lactide-co-glycolide) ("PLG"), or a copolymer of D,L-lactide and caprolactone. Poly(D,L-lactide-co-glycolide) polymers include those having a lactide/glycolide molar ratio ranging, for example, from 20:80 to 80:20, 25:75 to 75:25, 40:60 to 60:40, or 55:45 to 45:55, and having a molecular weight ranging, for example, from 5,000 to 200,00 Daltons, 10,000 to 100,000 Daltons, 20,000 to 70,000 Daltons, or 40,000 to 50,000 Daltons.

Antigen, phospholipid and various optional supplementary components may independently be, for example: (a) adsorbed to the surface of the microparticles, (b) entrapped within the microparticles, (c) in solution, (d) adsorbed to separate populations of microparticles, and/or (e) entrapped within separate populations of microparticles.

According to a second aspect of the invention, an immunogenic composition is provided which comprises: (a) water; (b) a metabolizable oil; (c) an emulsifying agent; (d) an antigen; and (e) a phospholipid compound such as those described above, wherein the composition is an oil-in-water emulsion having oil and aqueous phases, and wherein the oil phase(s) is in the form of oil droplets, substantially all of which are less than 1 micron in diameter.

The antigen, phospholipid molecule and various supplementary components may independently be, for example: dissolved or dispersed within the oil phase(s) of the emulsion (including separate populations of oil droplets), dissolved or dispersed within the aqueous phase of the emulsion and/or disposed at the interfaces between aqueous and oil phases of the emulsion.

The metabolizable oil is typically selected from animal oils (including fish oils) and vegetable oils, more typically an unsaturated hydrocarbon having from 20-40 carbons, more typically, branched, polyunsaturated hydrocarbon having from 20-40 carbon atoms, for example, terpenoids such as squalene.

The emulsifying agent typically comprises at least one non-ionic surfactant, more typically fatty acid esters and/or fatty acid esters comprising a polyoxyethylene moiety, for example, sorbitan derivatives such as sorbitan fatty acid monoesters, sorbitan fatty acid sesquiesters, sorbitan fatty acid triesters, polyoxyethylene sorbitan fatty acid monoesters and polyoxyethylene sorbitan fatty acid triesters. In a more specific example, the emulsifying agent comprises polyoxyethylene sorbitan monooleate and sorbitan trioleate. Where the emulsifying agent includes two or more surfactants, one surfactant can have, for example, an HLB value ranging from 1 to 9, while the other surfactant can have an HLB value ranging from 10 to 20.

Supplementary components can be included within the various compositions of the present invention, including pharmaceuticals, hormones, enzymes, transcription or translation mediators, metabolic pathway intermediates, immunomodulators, additional immunological adjuvants, and combinations thereof.

Antigens can be, for instance, polypeptide containing antigens or polynucleotide containing antigens. Examples of polynucleotide-containing antigens include, for example, (a) nucleic acid sequences that directly encode a polypeptide-containing antigens (e.g., an mRNA molecule) and (b) vector constructs that indirectly encode polypeptide-containing antigens, for example, vector constructs that express heterologous nucleic acid sequences, which in turn encode polypeptide-containing antigens (e.g., DNA vector constructs and RNA vector constructs).

Polypeptide-containing antigens can be, for example, tumor antigens and antigens from pathogenic organisms, such as viruses, bacteria, fungi and parasites. Thus, in some embodiments, the polypeptide-containing antigen is derived from a virus such as, for example, hepatitis A virus (HAV), hepatitis B virus (HBV), hepatitis C virus (HCV), herpes simplex virus (HSV), human immunodeficiency virus (HIV), cytomegalovirus (CMV), influenza virus (e.g., influenza A virus), and rabies virus. In other embodiments, the polypeptide-containing antigen is derived from a bacterium such as, for example, cholera, diphtheria, tetanus, *streptococcus* (e.g., *streptococcus* A and B), pertussis, *Neisseria meningitidis* (e.g., meningitis A, B, C, W, Y), *Neisseria gonorrhoeae*, *Helicobacter pylori*, and *Haemophilus influenza* (e.g., *Haemophilus influenza* type B). In still other embodiments, the polypeptide-containing antigen is derived from a parasite such as, for example, a malaria parasite.

Other embodiments of the invention are directed to methods of delivering antigens to a host animal, which comprises administering to the host animal any of the immunogenic compositions described herein. The host animal is preferably a vertebrate animal, more preferably a mammal, and even more preferably a human.

The present invention is also directed to methods of stimulating a humoral immune response and/or a cellular immune response, including a Th1 immune response, or a CTL response, or lymphoproliferation, or cytokine production, within a host animal in a host animal, comprising administering to the animal any of the immunogenic compositions described herein in an amount effective to induce the humoral and/or cellular immune response.

In other embodiments, the invention is directed to methods of immunization, which comprise administering to a host animal a therapeutically effective amount of any of the immunogenic compositions described herein.

The present invention is further directed to methods of immunizing a host animal, e.g., against a tumor or a viral, bacterial, or parasitic infection, comprising administering to the animal any of the immunogenic compositions described herein in an amount effective to induce a protective response.

Delivery of the immunogenic compositions of the invention may be performed by any known method, including direct injection (e.g., subcutaneously, intraperitoneally, intravenously or intramuscularly).

Hence, according to some embodiments of the present invention, compositions and methods are provided which treat, including prophylactically and/or therapeutically immunize, a host animal, e.g., against viral, fungal, mycoplasma, bacterial, or protozoan infections, as well as against tumors. The methods of the present invention are useful for conferring prophylactic and/or therapeutic immunity to a host animal, preferably a human. The methods of the present invention can also be practiced on animals other than humans, including biomedical research applications.

Other embodiments of the present invention are directed to methods for producing the above compositions. For example, the above polymer microparticles can be produced by a method that comprises: (a) forming a water-in-oil-in-water emulsion comprising water, organic solvent, biodegradable polymer, and anionic, cationic, nonionic or zwitterionic surfactant; and (b) removing the organic solvent from the emulsion, to form the polymer microparticles.

As another example, the above emulsions can be produced by a method that comprises: (a) providing a mixture comprising: organic solvent, water, metabolizable oil, and emulsifying agent; and (b) subjecting this mixture to sufficient shear stresses to produce an oil-in-water emulsion in which the oil phase(s) is in the form of oil droplets, substantially all of which are less than 1 micron in diameter.

One particular advantage of the immunogenic compositions of the present invention is the ability to generate immune responses in a vertebrate subject. In addition to a conventional antibody response, the compositions herein described can provide for, e.g., the association of the expressed antigens with class I MHC molecules such that an in vivo cellular immune response to the antigen of interest can be mounted, which stimulates the production of cytolytic T-cells ("CTLs") to allow for future recognition of the antigen. Furthermore, an antigen-specific response by helper T-cells may be elicited. Accordingly, the methods of the present invention will find use in eliciting cellular and/or humoral immune responses to a variety of antigens. As a specific example, antigens derived from viral pathogens can induce antibodies, T-cell helper epitopes and T-cell cytotoxic epitopes. Such antigens include those encoded by human and animal viruses and can correspond to either structural or non-structural proteins.

These and other embodiments, aspects and advantages of the present invention will become readily apparent to those of ordinary skill in the art in view of the disclosure herein.

DETAILED DESCRIPTION OF THE INVENTION

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S., ed, CRC Press, 1997) and *Seymour/Carraher=s Polymer Chemistry* (4th edition, Marcel Dekker Inc., 1996).

All publications, patents and patent applications cited herein, whether supra or infra, are hereby incorporated by reference in their entirety.

As used in this specification and any appended claims, the singular forms "a," "an" and "the" include plural references unless the content clearly dictates otherwise. Thus, for example, the term "microparticle" refers to one or more microparticles, and the like.

Unless stated otherwise, all percentages and ratios herein are given on a weight basis.

A. DEFINITIONS

In describing the present invention, the following terms will be employed, and are intended to be defined as indicated below.

The term "microparticle" as used herein, refers to a particle of about 10 nm to about 150 µm in diameter, more typically about 200 nm to about 30 µm in diameter, and even more typically about 500 nm to about 10-20 µm in diameter. The microparticles of the present invention may aggregate into larger masses under some circumstances. As a specific example, the microparticles of the present invention having adsorbed DNA may be, for instance, about 0.5-2 µm in diameter pre-lyophilization, while the same particles may be, for instance, in aggregates having a diameter of about 5-15 µm post-lyophilization. The microparticle will generally be of a diameter that permits parenteral or mucosal administration without occluding needles and capillaries. Microparticle size is readily determined by techniques well known in the art, such as photon correlation spectroscopy, laser diffractometry and/or scanning electron microscopy. The term "particle" may also be used to denote a microparticle as defined herein.

Polymer microparticles for use herein are typically formed from materials that are sterilizable, substantially non-toxic, and biodegradable. Such materials include biodegradable polymers such as poly(α-hydroxy acids), polyhydroxybutyric acids, polycaprolactones, polyorthoesters, polyanhydrides, and polycyanoacrylates (e.g., polyalkylcyanoacrylate or "PACA"). More typically, microparticles for use with the present invention are polymer microparticles derived from poly(α-hydroxy acids), for example, from a poly(lactide) ("PLA") or a copolymer of lactide and glycolide, such as a poly(D,L-lactide-co-glycolide) ("PLG"), or a copolymer of D,L-lactide and caprolactone. The polymer microparticles may be derived from any of various polymeric starting materials which have a variety of molecular weights and, in the case of the copolymers such as PLG, a variety of monomer (e.g., lactide:glycolide) ratios, the selection of which will be largely a matter of choice, depending in part on the coadministered species. These parameters are discussed further below.

The term "surfactant" as used herein includes detergents, dispersing agents, suspending agents, and emulsion stabilizers. Cationic surfactants for use in the polymer microparticle compositions of the present invention include, but are not limited to, cetyltrimethylammonium bromide or "CTA B" (e.g., cetrimide), benzalkonium chloride, DDA (dimethyl dioctodecyl ammonium bromide), DOTAP (dioleoyl-3-trimethylammonium-propane), and the like. Anionic surfactants include, but are not limited to, SDS (sodium dodecyl sulfate), SLS (sodium lauryl sulfate), DSS (disulfosuccinate), sulphated fatty alcohols, and the like. Nonionic surfactants include, but are not limited to, PVA, povidone (also known as polyvinylpyrrolidone or PVP), sorbitan esters, polysorbates, polyoxyethylated glycol monoethers, polyoxyethylated alkyl phenols, poloxamers, and the like.

The term "submicron emulsion" as used herein refers to an oil-in-water emulsion comprising oil droplets, substantially all of which range in size up to 1000 nm, for example, from 10 nm to 1000 nm.

The term "pharmaceutical" refers to biologically active compounds such as antibiotics, antiviral agents, growth factors, hormones, antigens and the like.

The term "adjuvant" refers to any substance that assists or modifies the action of a pharmaceutical, including but not limited to immunological adjuvants, which increase or diversify the immune response to an antigen. Hence, immunological adjuvants are compounds that are capable of potentiating an immune response to antigens. Immunological adjuvants can potentiate humoral and/or cellular immunity.

A "polynucleotide" is a nucleic acid polymer. A polynucleotide can include as little as 5, 6, 7 or 8 nucleotides. Furthermore, a "polynucleotide" can include both double- and single-stranded sequences and refers to, but is not limited to, cDNA from viral, procaryotic or eucaryotic mRNA, genomic RNA and DNA sequences from viral (e.g. RNA and DNA viruses and retroviruses) or procaryotic DNA, and synthetic DNA sequences. The term also captures sequences that include any of the known base analogs of DNA and RNA. The term further includes modifications, such as deletions, additions and substitutions (generally conservative in nature), to a native sequence, for example, where the nucleic acid molecule encodes an antigenic protein. These modifications may be deliberate, as through site-directed mutagenesis, or may be accidental, such as through mutations of hosts that produce antigens.

As used herein, the phrase "nucleic acid" refers to DNA, RNA, or chimeras formed therefrom.

A "polynucleotide-containing species" is a molecule, at least a portion of which is a polynucleotide. Examples include RNA vector constructs, DNA vector constructs and so forth.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to a native sequence, for example, such that the protein maintains the ability to elicit an immunological response or have a therapeutic effect on a subject to which the protein is administered.

A "polypeptide-containing species" is a molecule, at least a portion of which is a polypeptide. Examples include polypeptides, proteins including glycoproteins, saccharide antigens conjugated to carrier proteins, and so forth.

By "antigen" is meant a molecule that contains one or more epitopes capable of stimulating a host's immune system to make a cellular antigen-specific immune response when the antigen is presented, or a humoral antibody response. An antigen may be capable of eliciting a cellular and/or humoral response by itself or when present in combination with another molecule.

An "epitope" is that portion of an antigenic molecule or antigenic complex that determines its immunological specificity. An epitope is within the scope of the present definition of antigen. Commonly, an epitope is a polypeptide or polysaccharide in a naturally occurring antigen. In artificial antigens it can be a low molecular weight substance such as an arsanilic acid derivative. An epitope will react specifically in vivo or in vitro with, for example, homologous antibodies or T lymphocytes. Alternative descriptors are antigenic determinant, antigenic structural grouping and haptenic grouping.

Typically, an epitope will include between about 5-15 amino acids. Epitopes of a given protein can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by, for example, concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871;

Geysen et al. (1984) *Proc. Natl. Acad. Sci. USA* 81:3998-4002; Geysen et al. (1986) *Molec. Immunol.* 23:709-715. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra.

The term "antigen" as used herein denotes both subunit antigens, i.e., antigens which are separate and discrete from a whole organism with which the antigen is associated in nature, as well as killed, attenuated or inactivated bacteria, viruses, parasites or other pathogens or tumor cells. Antibodies such as anti-idiotype antibodies, or fragments thereof, and synthetic peptide mimotopes, which can mimic an antigen or antigenic determinant, are also captured under the definition of antigen as used herein.

Similarly, an oligonucleotide or polynucleotide that expresses an immunogenic protein, or antigenic determinant in vivo, such as in nucleic acid immunization applications, is also included in the definition of antigen herein.

Furthermore, for purposes of the present invention, an "antigen" refers to a protein, which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

An "immunological response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition such as an immunogenic composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al., *J. Immunol.* (1993) 151:4189-4199; Doe et al., *Eur. J. Immunol.* (1994) 24:2369-2376; and the examples below.

The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art, for instance, radioimmunoassays and ELISAs.

The immunogenic compositions of the present invention display "enhanced immunogenicity" when they possess a greater capacity to elicit an immune response than the immune response elicited by an equivalent amount of the antigen in a differing composition. Thus, a composition may display "enhanced immunogenicity," for example, because the composition generates a stronger immune response, or because a lower dose of antigen is necessary to achieve an immune response in the subject to which it is administered. Such enhanced immunogenicity can be determined, for example, by administering the compositions of the invention, and antigen controls, to animals and comparing assay results of the two.

As used herein, "treatment" (including variations thereof, for example, "treat" or "treated") refers to any of (i) the prevention of a pathogen or disorder in question (e.g. cancer or a pathogenic infection, as in a traditional vaccine), (ii) the reduction or elimination of symptoms, and (iii) the substantial or complete elimination of the pathogen or disorder in question. Treatment may be effected prophylactically (prior to arrival of the pathogen or disorder in question) or therapeutically (following arrival of the same).

The terms "effective amount" or "pharmaceutically effective amount" of an immunogenic composition of the present invention refer herein to a sufficient amount of the immunogenic composition to treat or diagnose a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

By "vertebrate subject" or "vertebrate animal" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are covered.

By "pharmaceutically acceptable" or "pharmacologically acceptable" is meant a material which is not biologically or otherwise undesirable, i.e., the material may be administered to an individual without causing any excessively undesirable biological effects in the individual or interacting in an excessively deleterious manner with any of the components of the composition in which it is contained.

The term "excipient" refers to any essentially accessory substance that may be present in the finished dosage form. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

By "physiological pH" or a "pH in the physiological range" is meant a pH in the range of approximately 7.2 to 8.0 inclusive, more typically in the range of approximately 7.2 to 7.6 inclusive.

As used herein, the phrase "vector construct" generally refers to any assembly that is capable of directing the expression of a nucleic acid sequence(s) or gene(s) of interest. A vector construct typically includes transcriptional promoter/enhancer or locus defining element(s), or other elements which control gene expression by other means such as alternate splicing, nuclear RNA export, post-translational modification of messenger, or post-transcriptional modification of protein. In addition, the vector construct typically includes a sequence which, when transcribed, is operably linked to the sequence(s) or gene(s) of interest and acts as a translation initiation sequence. The vector construct may also optionally include a signal that directs polyadenylation, a selectable marker, as well as one or more restriction sites and a translation termination sequence. In addition, if the vector construct is placed into a retrovirus, the vector construct may include a packaging signal, long terminal repeats (LTRs), and positive and negative strand primer binding sites appropriate to the retrovirus used (if these are not already present).

A "DNA vector construct" refers to a DNA molecule that is capable of directing the expression of a nucleic acid sequence(s) or gene(s) of interest.

One specific type of DNA vector construct is a plasmid, which is a circular episomal DNA molecule capable of autonomous replication within a host cell. Typically, a plasmid is a circular double stranded DNA loop into which additional DNA segments can be ligated. pCMV is one specific plasmid that is well known in the art. A preferred pCMV vector is one which contains the immediate-early enhancer/promoter of CMV and a bovine growth hormone terminator. It is described in detail in Chapman, B. S., et al. 1991. "Effect of intron A from human cytomegalovirus (Towne) immediate-early gene on heterologous expression in mammalian cells." Nucleic Acids Res. 19:3979-86.

Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. The RNA vector construct preferably comprises an RNA genome from a picornavirus, togavirus, flavivirus, coronavirus, paramyxovirus, yellow fever virus, or alphavirus (e.g., Sindbis virus, Semliki Forest virus, Venezuelan equine encephalitis virus, or Ross River virus), which has been modified by the replacement of one or more structural protein genes with a selected heterologous nucleic acid sequence encoding a product of interest. The RNA vector constructs can be obtained by transcription in vitro from a DNA template. Specific examples include Sindbis-virus-based plasmids (pSIN) such as pSINCP, described, for example, in U.S. Pat. Nos. 5,814,482 and 6,015,686, as well as in International Patent Applications WO 97/38087, WO 99/18226 and commonly owned WO 02/26209. The construction of such vectors, in general, is described in U.S. Pat. Nos. 5,814,482 and 6,015,686.

Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

B. GENERAL METHODS

1. Phospholipids

Phospholipid compounds are used in connection with the present invention. Examples include synthetic phospholipid compounds comprising: (a) one or more phosphoryl groups (wherein a phosphoryl group is represented by the radical =P=O), typically independently selected from a phosphato group,

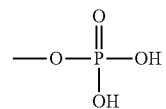

and a phosphodiester group

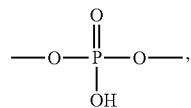

and (b) a plurality (typically, three to ten, more typically four to eight, even more typically six) of linear alkane groups,

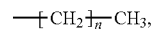

in which n is independently an integer ranging from 6 to 18, i.e., 6, 7, 8, 9, 10, 11, 12, 13, 14, 15, 16, 17 or 18, as well as pharmaceutically acceptable salts thereof. In certain embodiments, at least three, and in other embodiments at least four, of the alkane groups will independently be associated with alkanoyl groups, i.e.,

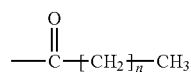

groups.

In certain embodiments, a plurality, and in other embodiments at least two, three or four, of the alkane groups will correspond to alkanoyloxy groups, i.e.,

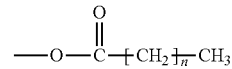

groups, which can further correspond, for example, to alkanoyloxy-alkoxy groups, e.g.

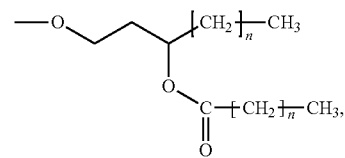

or to alkanoyloxy-alkanoyl groups, e.g.,

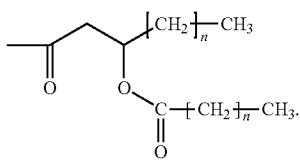

In certain embodiments, the phospholipid compound contains, two, three, four or more diphosphoryl groups. For example, the phospholipid compound can be a diphosphato phospholipid compound, or a di-phosphodiester phospholipid compound.

In numerous embodiments, the phospholipid compound does not comprise a glucosamine disaccharide group, e.g.,

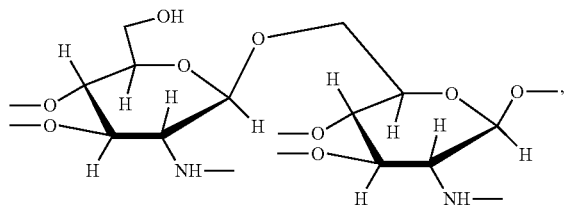

or even a single glucosamine saccharide group, e.g.,

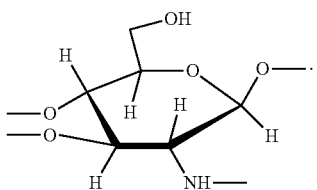

In still others, the phospholipid compound does not comprise any saccharide group whatsoever.

One example of a family of phospholipid compounds for use in the present invention is the family of phospholipid compounds having the following formula:

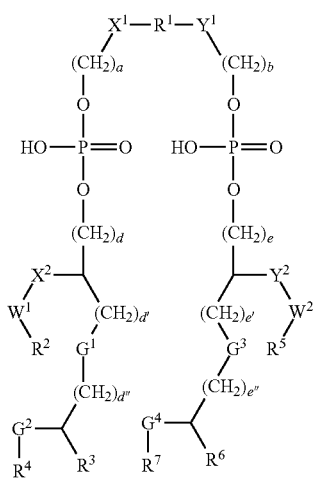

wherein:
$R^1$ is selected from the group consisting of
(a) C(O);
(b) C(O)—$C_{1-14}$ alkyl-C(O), wherein the $C_{1-14}$ alkyl is optionally substituted with hydroxy, $C_{1-5}$ alkoxy, $C_{1-5}$ alkylenedioxy, $C_{1-5}$ alkylamino, or $C_{1-5}$-alkyl-aryl, wherein the aryl moiety of the $C_{1-5}$-alkyl-aryl is optionally substituted with $C_{1-5}$ alkoxy, $C_{1-5}$ alkylamino, $C_{1-5}$ alkoxy-amino, $C_{1-5}$ alkylamino-$C_{1-5}$ alkoxy, —O—$C_{1-5}$ alkylamino-$C_{1-5}$ alkoxy, —O—$C_{1-5}$ alkylamino-C(O)—$C_{1-5}$ alkyl C(O)OH, —O—$C_{1-5}$ alkylamino-C(O)—$C_{1-5}$ alkyl-C(O)—$C_{1-5}$ alkyl;
(c) $C_2$ to $C_{15}$ straight or branched chain alkyl optionally substituted with hydroxy or alkoxy; and
(d) —C(O)—$C_{6-12}$ arylene-C(O)— wherein the arylene is optionally substituted with hydroxy, halogen, nitro or amino;
a and b are independently 0, 1, 2, 3 or 4;
d, d', d", e, e' and e" are independently an integer from 1 to 4;
$X^1$, $X^2$, $Y^1$ and $Y^2$ are independently selected from the group consisting of a null, oxygen, NH and N(C(O)$C_{1-4}$ alkyl), and N($C_{1-4}$ alkyl)$_2$;
$W^1$ and $W^2$ are independently selected from the group consisting of carbonyl, methylene, sulfone and sulfoxide;
$R^2$ and $R^5$ are independently selected from the group consisting of:
(a) $C_2$ to $C_{20}$ straight chain or branched chain alkyl which is optionally substituted with oxo, hydroxy or alkoxy,
(b) $C_2$ to $C_{20}$ straight chain or branched chain alkenyl or dialkenyl which is optionally substituted with oxo, hydroxy or alkoxy;
(c) $C_2$ to $C_{20}$ straight chain or branched chain alkoxy which is optionally substituted with oxo, hydroxy or alkoxy;
(d) —NH—$C_2$ to $C_{20}$ straight chain or branched chain alkyl, wherein the alkyl group is optionally substituted with oxo, hydroxy or alkoxy; and
(e)

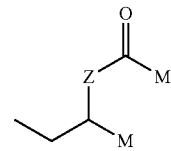

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;
$R^3$ and $R^6$ are independently selected from the group consisting of $C_2$ to straight chain or branched chain alkyl or alkenyl, optionally substituted with fluoro or oxo;
$R^4$ and $R^7$ are independently selected from the group consisting of C(O)$C_2$ to $C_{20}$ straight chain or branched chain alkyl or alkenyl; $C_2$ to $C_{20}$ straight chain or branched chain alkyl; $C_2$ to $C_{20}$ straight chain or branched chain alkoxy; $C_2$ to $C_{20}$ straight chain or branched chain alkenyl; wherein the alkyl, alkenyl or alkoxy groups are independently and optionally substituted with hydroxy, fluoro or $C_1$ to $C_5$ alkoxy;
$G^1$, $G^2$, $G^3$ and $G^4$ are independently selected from the group consisting of oxygen, methylene, amino, thiol, —NHC(O)—, and —N(C(O)$C_{1-4}$ alkyl)-; or $G^2$ $R^4$ or $G^4$ $R^7$ may together be a hydrogen atom or hydroxyl;
or a pharmaceutically acceptable salt thereof.
In some specific embodiments, R' is C(O); a, b d, d', d", e e' and e" are independently 1 or 2; $X^1$, $X^2$, $Y^1$ and $Y^2$ are NH; $W^1$ and $W^2$ are carbonyl; $R^2$ and $R^5$ are $C_{10}$ to $C_{70}$ straight chain alkyl which is substituted with oxo; $R^3$ and $R^6$ are $C_5$-$C_{10}$ straight chain alkyl; $R^4$ and $R^7$ are C(O)$C_8$-$C_{11}$ straight chain alkyl; and $G^1$, $G^2$, $G^3$ and $G^4$ are oxygen.

An example of a specific compound for use in connection with the present invention is the following compound:

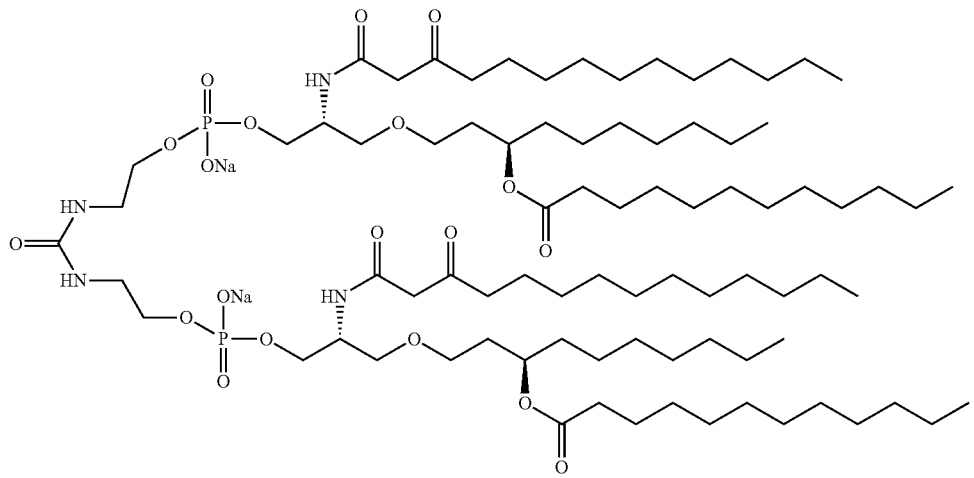

The compound illustrated is in the (R,R,R,R) enantiomeric form, but other enantiomeric forms including the (R,S,S,R) form are also desirable. These compounds are synthetic compounds from Eisai Co. Ltd., Tokyo, Japan and are designated ER804057 and ER804053. They are members of the above family of phospholipids, in sodium salt form, where: $R^1$ is C(O); a and b are 2; d, d', e and e' are 1; d" and e" are 2; $X^1$, $X^2$, $Y^1$ and $Y^2$ are NH; $W^1$ and $W^2$ are carbonyl; $R^2$ and $R^5$ are $C_{13}$ straight chain alkyl which is substituted with oxo at the 2 position; $R^3$ and $R^6$ are $C_7$ straight chain alkyl; $R^4$ and $R^7$ are $C(O)C_{11}$ straight chain alkyl; $G^1$, $G^2$, $G^3$ and $G^4$ are oxygen. This compound does not comprise any saccharide groups; it is a diphospholipid compound, as it comprises two phosphodiester group

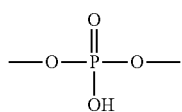

(here, in the sodium salt form). This compound also comprises six linear alkane groups,

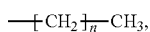

in which n is independently or 6 or 10. Four of the alkane groups correspond to alkanoyl groups,

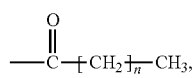

where n is 10. Two of these alkanoyl groups correspond to alkanoyloxy groups,

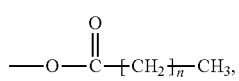

which further correspond to alkanoyloxyalkoxy groups,

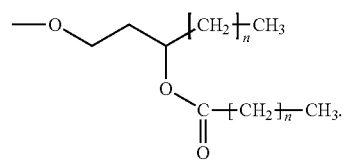

Further information concerning the above compounds and their preparation can be found, for example, in U.S. Pat. No. 6,290,973 to Eisai Co., Ltd.

2. Antigens

The present invention will find use for stimulating an immune response against a wide variety of antigens, including antigens associated with pathogens and tumors.

Antigens from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7 can be conveniently used in connection with the present invention. (See, e.g. Chee et al., *Cytomegaloviruses* (J. K. McDougall, ed., Springer-Verlag 1990) pp. 125-169, for a review of the protein coding content of cytomegalovirus; McGeoch et al., *J. Gen. Virol.* (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207-211, for the identification of protein coding sequences in an EBV genome; and Davison and Scott, *J. Gen. Virol.* (1986) 67:1759-1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NS1) and an N-terminal nucleocapsid protein (termed "core") (see, Houghton et al., *Hepatology* (1991) 14:381-388, for a discussion of HCV proteins, including E1 and E2). Each of these proteins, as well as antigenic fragments thereof, will find use in the present composition and methods.

Similarly, the sequence for the δ-antigen from HDV is known (see, e.g., U.S. Pat. No. 5,378,814) and this antigen can also be conveniently used in the present composition and methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines—from the laboratory to license: a case study" in Mackett, M. and Williamson, J. D., *Human Vaccines and Vaccination*, pp. 159-176, for a discussion of HBV structure; and U.S. Pat. Nos. 4,722,840, 5,098,704, 5,324,513, incorporated herein by reference in their entireties; Beames et al., *J. Virol.* (1995) 69:6833-6838, Birnbaum et al., *J. Virol.* (1990) 64:3319-3330; and Zhou et al., *J. Virol.* (1991) 65:5457-5464.

Antigens derived from other viruses, will also find use in the compositions and methods of the present invention, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); *Fundamental Virology*, 2nd Edition (B. N. Fields and D. M. Knipe, eds. 1991), for a description of these and other viruses.

More particularly, the gp120 or gp140 envelope proteins from any of the above HIV isolates, including members of the various genetic subtypes of HIV, are known and reported (see, e.g., Myers et al., Los Alamos Database, Los Alamos National Laboratory, Los Alamos, N. Mex. (1992); Myers et al., *Human Retroviruses and Aids*, 1990, Los Alamos, N. Mex.: Los Alamos National Laboratory; and Modrow et al., *J. Virol.* (1987) 61:570-578, for a comparison of the envelope sequences of a variety of HIV isolates) and antigens derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol and tat regions.

Influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759-767; Webster et al., "Antigenic variation among type A influenza viruses," p. 127-168. In: P. Palese and D. W. Kingsbury (ed.), *Genetics of influenza viruses*. Springer-Verlag, New York). Thus, proteins derived from any of these isolates can also be used in the compositions and methods described herein.

The compositions and methods described herein will also find use with numerous bacterial antigens, such as those derived from organisms that cause diphtheria, cholera, tuberculosis, tetanus, pertussis, meningitis, and other pathogenic states, including, without limitation, *Bordetella pertussis*, *Neisseria meningitides* (A, B, C, Y), *Neisseria gonorrhoeae*, *Helicobacter pylori*, and *Haemophilus influenza*. *Hemophilus influenza* type B (HIB), *Helicobacter pylori*, and combinations thereof. Examples of antigens from *Neisseria meningitides* B are disclosed in the following co-owned patent applications: PCT/US99/09346; PCT IB98/01665; and PCT IB99/00103. Examples of parasitic antigens include those derived from organisms causing malaria and Lyme disease.

Additional antigens for use with the invention, which are not necessarily exclusive of those listed elsewhere in this application, include the following: (a) a protein antigen from *N. meningitidis* serogroup B, such as those in Refs. 1 to 7 below; (b) an outer-membrane vesicle (OMV) preparation from *N. meningitidis* serogroup B, such as those disclosed in Refs. 8, 9, 10, 11, etc. below; (c) a saccharide antigen from *N. meningitidis* serogroup A, C, W135 and/or Y, such as the oligosaccharide disclosed in Ref. 12 below from serogroup C (see also Ref. 13); (d) a saccharide antigen from *Streptococcus pneumoniae* [e.g. Refs. 14, 15, 16]. (e) an antigen from *N. gonorrhoeae* [e.g., Refs. 1, 2, 3]; (e) an antigen from *Chlamydia pneumoniae* [e.g., Refs. 17, 18, 19, 20, 21, 22, 23]; (D an antigen from *Chlamydia trachomatis* [e.g. Ref. 24]; (g) an antigen from hepatitis A virus, such as inactivated virus [e.g., Refs. 25, 26]; (h) an antigen from hepatitis B virus, such as the surface and/or core antigens [e.g., Refs. 26, 27]; (i) an antigen from hepatitis C virus [e.g. Ref. 28]; (j) an antigen from *Bordetella pertussis*, such as pertussis holotoxin (PT) and filamentous haemaglutinin (FHA) from *B. pertussis*, optionally also in combination with pertactin and/or agglutinogens 2 and 3 [e.g., Refs. 29 & 30]; (k) a diphtheria antigen, such as diphtheria toxoid [e.g., chapter 3 of Ref. 31] e.g. the $CRM_{197}$ mutant [e.g., Ref. 32]; (l) a tetanus antigen, such as a tetanus toxoid [e.g., chapter 4 of Ref. 31]; (m) a protein antigen from *Helicobacter pylori* such as CagA [e.g. Ref. 33], VacA [e.g. Ref. 33], NAP [e.g. Ref. 34], HopX [e.g. Ref. 35], HopY [e.g. Ref. 35] and/or urease; (n) a saccharide antigen from *Haemophilus influenzae* B [e.g. Ref. 13]; (o) an antigen from *Porphyramonas gingivalis* [e.g. Ref. 36]; (p) polio antigen(s) [e.g. Refs. 37, 38] such as IPV or OPV; (q) rabies antigen(s) [e.g. Ref. 39] such as lyophilized inactivated virus [e.g. Ref. 40, Rabavert™); (r) measles, mumps and/or rubella antigens [e.g., chapters 9, 10 and 11 of Ref. 31]; (s) influenza antigen(s) [e.g. chapter 19 of Ref. 31], such as the haemagglutinin and/or neuraminidase surface proteins; (t) an antigen from *Moraxella catarrhalis* [e.g., time 41]; (u) an antigen from *Streptococcus agalactiae* (Group B *streptococcus*) [e.g. Refs. 42, 43]; (v) an antigen from *Streptococcus pyogenes* (Group A *streptococcus*) [e.g. Refs. 43, 44, 45]; (w) an antigen from *Staphylococcus aureus* [e.g. Ref. 46]; and (x) compositions comprising one or more of these antigens. Where a saccharide or carbohydrate antigen is used, it is preferably conjugated to a carrier protein in order to enhance immunogenicity [e.g. Refs. 47 to 56]. Preferred carrier proteins are bacterial toxins or toxoids, such as diphtheria or tetanus toxoids. The $CRM_{197}$ diphtheria toxoid is particularly preferred. Other suitable carrier proteins include *N. meningitidis* outer membrane protein [e.g. Ref. 57], synthetic peptides [e.g. Refs. 58, 59], heat shock proteins [e.g. Ref. 60], pertussis proteins [e.g. Refs. 61, 62], protein D from *H. Influenzae* [e.g. Ref. 63], toxin A or B from *C. difficile* [e.g. Ref. 64], etc. Where a mixture comprises capsular saccharides from both serogroups A and C, it is preferred that the ratio (w/w) of MenA saccharide:MenC saccharide is greater than 1 (e.g. 2:1, 3:1, 4:1, 5:1, 10:1 or higher). Saccharides from different serogroups of *N. meningitidis* may be conjugated to the same or different carrier proteins. Any suitable conjugation reaction can be used, with any suitable linker where necessary. Toxic protein antigens may be detoxified where necessary (e.g. detoxification of pertussis toxin by chemical and/or means [Ref. 30]. See: International patent application 99/24578 [Ref. 1]; International patent application WO99/36544 [Ref. 2]; International patent application WO99/57280 [Ref. 3]; International patent application WO00/22430 [Ref. 4]; Tettelin et al., (2000) *Science* 287:1809-1815 [Ref. 5]; International patent application WO96/29412 [Ref. 6]; Pizza et al. (2000) *Science* 287:1816-1820 [Ref. 7]; International patent application PCT/IBOI/00166 [Ref. 8]; Bjune et al. (1991) *Lancet* 338(8775):1093-1096 [Ref. 9]; Fukasawa et al. (1990) *Vaccine* 17:2951-2958 [Ref. 10]; Rosenqvist et al. (1998) *Dev. Biol. Stand.* 92:323-333 [Ref. 11]; Costantino et al. (1992) *Vaccine* 10:691-698 [Ref. 12]; Costantino et al. (1999) *Vaccine* 17:1251-1263 [Ref. 13]; Watson (2000) *Padiatr Infect Dis J* 19:331-332 [Ref. 14]; Rubin (2000) *Pediatr Clin North Am* 47:269-285, v [Ref. 15]; Jedrzejas (2001) *Microbiol Mol Biol Rev* 65:187-207 [Ref. 16]; International patent application filed on 3 Jul. 2001 claiming priority from GB-0016363.4 [Ref. 17]; Kalman et al. (1999) *Nature Genetics* 21:385-389 [Ref. 18]; Read et al. (2000) *Nucleic Acids Res* 28:1397-406 [Ref. 19]; Shirai et al. (2000) *J. Infect. Dis.* 181(Suppl 3):S524-S527 [Ref. 20]; International patent application WO99/27105 [Ref. 21]; International patent application WO00/27994 [Ref. 22]; International patent application WO00/37494 [Ref. 23]; International patent application WO99/28475 [Ref. 24]; Bell (2000) *Pediatr Infect Dis J*19:1187-1188 [Ref. 25]; Iwarson (1995) *APMIS* 103:321-326 [Ref. 26]; Gerlich et al. (1990) *Vaccine* 8 Suppl:S63-68 & 79-80 [Ref. 27]; Hsu et al. (1999) *Clin Liver Dis* 3:901-915 [Ref. 28]; Gustafsson et al. (1996) *N. Engl. J. Med.* 334:349-355 [Ref. 29]; Rappuoli et al. (1991) *TIBTECH* 9:232-238 [Ref. 30]; *Vaccines* (1988) eds. Plotkin & Mortimer. ISBN 0-7216-1946-0 [Ref. 31]; Del Guidice et al. (1998) *Molecular Aspects of Medicine* 19:1-70 [Ref. 32]; International patent application WO93/18150 [Ref 33]; International patent application WO99/53310 [Ref. 34]; International patent application WO98/04702 [Ref. 35]; Ross et al. (2001) *Vaccine* 19:4135-4142 [Ref 36]; Sutter et al. (2000) *Pediatr Clin North Am* 47:287-308 [Ref 37]; Zimmerman & Spann (1999) *Am Fam Physician* 59:113-118, 125-126 [Ref 38]; Dreesen (1997) *Vaccine* 15 Suppl:S2-6 [Ref 39]; *MMWR Morb Mortal Wkly Rep* 1998 Jan. 16; 47(1):12, 19 [Ref 40]; McMichael (2000) *Vaccine* 19 Suppl 1:S101-107 [Ref 41]; Schuchat (1999) *Lancet* 353(9146):51-6 [Ref 42]; GB patent applications 0026333.5, 0028727.6 & 0105640.7 [Ref 43]; Dale (1999) *Infect Dis Clin North Am* 13:227-43, viii [Ref 44]; Ferretti et al. (2001) *PNAS USA* 98:4658-4663 [Ref. 45]; Kuroda et al. (2001) *Lancet* 357(9264):1225-1240; see also pages 1218-1219 [Ref. 46]; Ramsay et al. (2001) *Lancet* 357(9251):195-196 [Ref 47]; Lindberg (1999) *Vaccine* 17 Suppl 2:S28-36 [Ref 48]; Buttery & Moxon (2000) *J R Coll Physicians London* 34:163-168 [Ref 49]; Ahmad & Chapnick (1999) *Infect Dis Clin North Am* 13:113-133, vii [Ref. 50]; Goldblatt (1998) *J. Med. Microbiol.* 47:563-567 [Ref 51]; European patent 0 477 508 [Ref. 52]; U.S. Pat. No. 5,306,492 [Ref 53]; International patent application WO98/42721 [Ref 54]; *Conjugate Vaccines* (eds. Cruse et al.) ISBN 3805549326, particularly vol. 10:48-114 [Ref. 55]; Hermanson (1996) *Bioconjugate Techniques* ISBN: 0123423368 & 012342335X [Ref 56]; European patent application 0372501 [Ref. 57]; European patent application 0378881 [Ref. 58]; European patent application 0427347 [Ref. 59]; International patent application WO93/17712 [Ref. 60]; International patent application WO98/58668 [Ref. 61]; European patent application 0471177 [Ref. 62]; International patent application WO00/56360 [Ref. 63]; international patent application WO00/61761 [Ref. 64].

Where diphtheria antigen is included in the composition it is preferred also to include tetanus antigen and pertussis antigens. Similarly, where a tetanus antigen is included it is preferred also to include diphtheria and pertussis antigen. Similarly, where a pertussis antigen is included it is preferred also to include diphtheria and tetanus antigens.

Additional antigens include antigens directed to plague, Rocky Mountain spotted fever, smallpox, typhoid, typhus, feline leukemia virus, and yellow fever.

3. Immunogenic Emulsion Compositions

Various embodiments of the present invention are directed to immunogenic emulsion compositions. In addition to phospholipid and antigen species (discussed above) as well as optional supplemental components (discussed below), the immunogenic emulsion compositions of the present invention beneficially comprise (a) water, (b) a metabolizable oil and (c) an emulsifying agent. Typically, the immunogenic emulsion is an oil-in-water emulsion in which substantially all of the oil droplets are smaller than 1 micron in diameter, more typically smaller than 250 nm. In certain embodiments, the composition exists in the absence of any polyoxypropylene-polyoxyethylene block copolymer.

These immunogenic emulsion compositions typically comprise 0.5 to 20% by volume oil, more typically 1 to 10% by volume oil, and even more typically 2 to 6% by volume oil; and 80 to 99.5% by volume water, more typically 90 to 99% by volume water. The compositions also typically comprise about 0.001 to about 5% by weight emulsifying agent, more typically 0.001 to 1%, by weight emulsifying agent, even more typically 0.01 to 0.1% by weight emulsifying agent; about 0.1 to 5% by weight phospholipid, more typically 0.5 to 1% by weight phospholipid; where a polypeptide-containing antigen is employed, about 0.1 to 5% by weight polypeptide-containing antigen, more typically 0.5 to 1% by weight polypeptide-containing antigen; and where a polynucleotide-containing antigen is employed, about 0.1 to 20% by weight polynucleotide-containing antigen, more typically about 1 to 10% by weight polynucleotide-containing antigen.

The metabolizable oil is commonly one having about 6 to about 30 carbon atoms including, but not limited to, alkanes, alkenes, alkynes, and their corresponding acids and alcohols, the ethers and esters thereof, and mixtures thereof. The oil can be essentially any vegetable oil, fish oil, animal oil or synthetically prepared oil which can be metabolized by the body of the host animal to which the immunogenic emulsion compositions will be administered, and which is not substantially toxic to the subject. Mineral oil and similar toxic petroleum distillate oils are excluded from this invention.

For example, the oil component of this invention can be any long chain alkane, alkene or alkyne, or an acid or alcohol derivative thereof, for example, as the free acid, its salt or an ester thereof, such as a mono-, or di- or tri-esters, for instance, triglycerides, esters of 1,2-propanediol or similar poly-hydroxy alcohols. Alcohols can be acylated employing amino- or poly-functional acid, for example acetic acid, propanoic acid, citric acid or the like. Ethers derived from long chain alcohols which are oils and meet the criteria set forth herein can also be used.

The individual alkane, alkene or alkyne moiety and its acid or alcohol derivatives will generally have about 6 to about 30 carbon atoms. The moiety can have a straight or branched chain structure. It can be fully saturated or have one or more double or triple bonds. Where mono or poly ester- or ether-based oils are employed, the limitation of about 6 to about 30 carbons applies to the individual fatty acid or fatty alcohol moieties, not the total carbon count.

As a specific example, many fish contain metabolizable oils which may be readily recovered. For instance, cod liver oil, shark liver oils, and whale oil such as spermaceti exemplify several of the fish oils, which may be used herein. A number of branched chain oils can be synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene. Fish oils, including squalene and squalane, the saturated analog to squalene, are readily available from commercial sources or may be obtained by methods known in the art.

A substantial number of suitable emulsifying agents (also referred to herein as surfactants, detergents and so forth) are used in the pharmaceutical sciences, many of which are useful in the immunogenic emulsion compositions of the present invention, so long as they are sufficiently non-toxic. These include naturally derived materials such as gums from trees, vegetable protein, sugar-based polymers such as alginates and cellulose, and the like. Certain oxypolymers or polymers having a hydroxide or other hydrophilic substituent on the carbon backbone have surfactant activity, for example, povidone, polyvinyl alcohol, and glycol ether-based mono- and poly-functional compounds. Long chain fatty-acid-derived compounds form another substantial group of emulsifying agents that could be used in this invention.

Specific examples of suitable emulsifying agents that can be used in accordance with the present invention include the following: (1) Water-soluble soaps, such as the sodium, potassium, ammonium and alkanol-ammonium salts of higher fatty acids ($C_{10}$-$C_{22}$), and, particularly sodium and potassium tallow and coconut soaps. (2) Anionic synthetic non-soap detergents, which can be represented by the water-soluble salts of organic sulfuric acid reaction products having in their molecular structure an alkyl radical containing from about 8 to 22 carbon atoms and a radical selected from the group consisting of sulfonic acid and sulfuric acid ester radicals.

(3) Nonionic synthetic detergents made by the condensation of alkylene oxide groups with an organic hydrophobic compound. Typical hydrophobic groups include condensation products of propylene oxide with propylene glycol, alkyl phenols, condensation product of propylene oxide and ethylene diamine, aliphatic alcohols having 8 to 22 carbon atoms, and amides of fatty acids.

(4) Nonionic detergents, such as amine oxides, phosphine oxides and sulfoxides, having semipolar characteristics. (5) Long chain sulfoxides, including those corresponding to the formula $R_1$—SO—$R_2$ wherein $R_1$ and $R_2$ are substituted or unsubstituted alkyl radicals, the former containing from about 10 to about 28 carbon atoms, whereas $R_2$ contains from 1 to 3 carbon atoms. (6) Ampholytic synthetic detergents, such as sodium 3-dodecylaminopropionate and sodium 3-dodecylaminopropane sulfonate. (7) Zwitterionic synthetic detergents, such as 3-(N,N-dimethyl-N-hexadecylammonio) propane-1-sulfonate and 3-(N,N-dimethyl-N-hexadecylammonio)-2-hydroxy propane-1-sulfonate.

The following types of emulsifying agents, which are not necessarily exclusive of those in the prior paragraph, can also be used in the immunogenic emulsion compositions of the present invention: (a) soaps (i.e., alkali salts) of fatty acids, rosin acids, and tall oil; (b) alkyl arene sulfonates; (c) alkyl sulfates, including surfactants with both branched-chain and straight-chain hydrophobic groups, as well as primary and secondary sulfate groups; (d) sulfates and sulfonates containing an intermediate linkage between the hydrophobic and hydrophilic groups, such as the fatty acylated methyl taurides and the sulfated fatty monoglycerides; (e) long-chain acid esters of polyethylene glycol, especially the tall oil esters; (f) polyethylene glycol ethers of alkylphenols; (g) polyethylene glycol ethers of long-chain alcohols and mercaptans; and (h) fatty acyl diethanol amides.

There are a number of emulsifying agents specifically designed for and commonly used in biological situations. For example, a number of biological detergents (surfactants) are listed as such by Sigma Chemical Company on pages 310-316 of its 1987 Catalog of Biochemical and Organic Compounds. Such surfactants are divided into four basic types: anionic, cationic, zwitterionic, and nonionic. Examples of anionic detergents include alginic acid, caprylic acid, cholic acid, 1-decanesulfonic acid, deoxycholic acid, 1-dodecane-sulfonic acid, N-lauroylsarcosine, and taurocholic acid. Cationic detergents include dodecyltrimethylammonium bromide, benzalkonium chloride, benzyldimethylhexadecyl ammonium chloride, cetylpyridinium chloride, methylbenzethonium chloride, and 4-picoline dodecyl sulfate. Examples of zwitterionic detergents include 3-[(3-cholamidopropyl)-dimethylammonio]-1-propanesulfonate (commonly abbreviated CHAPS), 3-[(cholamidopropyl)dimethylammonio]-2-hydroxy-1-propanesulfonate (commonly abbreviated CHAPSO), N-dodecyl-N,N-dimethyl-3-ammonio-1-propanesulfonate, and lyso-alpha-phosphatidylcholine. Examples of nonionic detergents include decanoyl-N-methylglucamide, diethylene glycol monopentyl ether, n-dodecyl beta-D-glucopyranoside, ethylene oxide condensates of fatty alcohols (e.g., those sold under the trade name Lubrol), polyoxyethylene ethers of fatty acids (particularly $C_{12}$-$C_{20}$ fatty acids), polyoxyethylene sorbitan fatty acid esters (e.g., sold under the trade name Tween®), and sorbitan fatty acid esters (e.g., sold under the trade name Span®).

A particularly useful group of surfactants are the sorbitan-based non-ionic surfactants. These surfactants are typically prepared by dehydration of sorbitol to give 1,4-sorbitan, which is then reacted with one or more equivalents of a fatty acid. The fatty-acid-substituted moiety may be further reacted with ethylene oxide to give a second group of surfactants.

The fatty-acid-substituted sorbitan surfactants are typically made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common names for some of these surfactants include, for example, sorbitan monolaurate, sorbitan monopalmitate, sorbitan monostearate, sorbitan monooleate, sorbitan sesquioleate, and sorbitan trioleate. These surfactants are commercially available under the names SPAN® or ARLACEL®.

SPAN® and ARLACEL® surfactants are lipophilic and are generally soluble or dispersible in oil. They are also soluble in most organic solvents. In water they are generally insoluble but dispersible. Generally these surfactants will have a hydrophilic-lipophilic balance (HLB) number between 1.8 and 8.6. Such surfactants can be readily made by means known in the art or are commercially available from, for example, ICI America's Inc., Wilmington, Del. under the registered mark ATLAS®.

A related group of surfactants comprises polyoxyethylene sorbitan monoesters and polyoxyethylene sorbitan triesters.

These materials are typically prepared by addition of ethylene oxide to a 1,4-sorbitan monoester or triester. The addition of polyoxyethylene converts the lipophilic sorbitan mono- or triester surfactant into a hydrophilic surfactant generally soluble or dispersible in water and soluble to varying degrees in organic liquids. The TWEEN® surfactants may be combined, for example, with a related sorbitan monoester or triester surfactant to promote emulsion stability. TWEEN® surfactants generally have a HLB value falling between 9.6 and 16.7. TWEEN® surfactants are commercially available from a number of manufacturers, for example ICI America's Inc., Wilmington, Del. under the registered mark ATLAS® surfactants.

Another group of non-ionic surfactants which could be used alone or in conjunction with SPAN®, ARLACEL® and/or TWEEN® surfactants are the polyoxyethylene fatty acids made by the reaction of ethylene oxide with a long-chain fatty acid. The most commonly available surfactant of this type is solid under the name MYRJ® and is a polyoxyethylene derivative of stearic acid. MYRJ® surfactants are hydrophilic and soluble or dispersible in water, like TWEEN® surfactants. The MYRJ® surfactants may be blended, for example, with TWEEN® surfactants or with TWEEN®/SPAN® or with ARLACEL® surfactant mixtures for use in forming emulsions. MYRJ® surfactants can be made by methods known in the art or are available commercially from ICI America's Inc.

Another group of polyoxyethylene based non-ionic surfactants are the polyoxyethylene fatty acid ethers derived from lauryl, acetyl, stearyl and oleyl alcohols. These materials are typically prepared as above by addition of ethylene oxide to a fatty alcohol. The commercial name for these surfactants is BRIJ®. BRIJ® surfactants may be hydrophilic or lipophilic depending on the size of the polyoxyethylene moiety in the surfactant. While the preparation of these compounds is available from the art, they are also readily available from such commercial sources as ICI America's Inc.

Other non-ionic surfactants which may be used in the practice of this invention are, for example: polyoxyethylenes, polyol fatty acid esters, polyoxyethylene ethers, polyoxypropylene fatty ethers, bee's wax derivatives containing polyoxyethylene, polyoxyethylene lanolin derivatives, polyoxyethylene fatty glycerides, glycerol fatty acid esters or other polyoxyethylene acid alcohols or ether derivatives of long-chain fatty acids of 12-22 carbon atoms.

As noted above, in certain embodiments, two or more surfactants are combined in the immunogenic emulsion compositions of the present invention. For instance, the immunogenic emulsion compositions can comprise a hydrophilic emulsifying agent having an HLB value ranging from 1-9 and a lipophilic emulsifying agent having an HLB value ranging from 10-18. As a specific example, a sorbitan fatty acid ester can be combined with a polyoxyethylene sorbitan fatty acid ester (see Table 1 below, which lists several of these emulsifiers, along with their associated HLB values).

TABLE 1

| Emulsifier | HLB |
|---|---|
| Sorbitan trioleate (Span ® 85) | 1.8 |
| Sorbitan tristearate (Span ® 65) | 2.1 |
| Sorbitan sesquioleate (Arlacel ® 83) | 3.7 |
| Sorbitan monooleate (Span ® 80) | 4.3 |
| Sorbitan monostearate (Span ® 60) | 4.7 |
| Sorbitan monopalmitate (Span ® 40) | 6.7 |
| Sorbitan monolaurate (Span ® 20) | 8.6 |
| Polyoxyethylene sorbitan tristearate (Tween ® 65) | 10.5 |

TABLE 1-continued

| Emulsifier | HLB |
|---|---|
| Polyoxyethylene sorbitan trioleate (Tween ® 85) | 11.0 |
| Polysorbate 60 (Tween ® 60) | 14.9 |
| Polysorbate 80 (Tween ® 80) | 15.0 |
| Polysorbate 40 (Tween ® 40) | 15.6 |
| Polysorbate 20 (Tween ® 20) | 16.7 |

Because the immunogenic emulsion compositions of the present invention are commonly intended for parenteral administration, the tonicity, i.e., osmolality, of the immunogenic compositions is typically compatible with normal physiological fluids in order to prevent post-administration swelling or rapid absorption of the composition due to, for example, differential solute concentrations between the composition and physiological fluids. Essentially any physiologically acceptable solute, for example, sodium chloride, can be used to adjust osmolality.

The emulsion compositions are also typically buffered in order to maintain pH compatible with normal physiological conditions. Also, in certain instances, it can be necessary to maintain the pH at a particular level in order to ensure the stability of certain composition components such as the glycopeptides. Any physiologically acceptable buffer can be used herein, such as phosphate buffers. Other acceptable buffers such acetate, Tris, bicarbonate, carbonate, or the like can be used as well. The pH of the aqueous component will typically be between about 6.0-8.0.

When the submicron emulsion is initially prepared unadulterated water is typically used as the aqueous component of the emulsion, because, for example, increasing salt concentration can make it more difficult to achieve the desired small droplet size.

Once the emulsion is prepared, however, the tonicity and the pH can be properly adjusted, for example, by the addition of solute and/or appropriate buffer. In some embodiments, the antigen can be added in a buffer solution having an osmolality and pH appropriate to provide the desired osmolality and pH to the final immunogenic composition. Similarly, in some embodiments, the phospholipid can be dissolved or dispersed in a buffer solution having an appropriate osmolality and pH and added to the emulsion.

The immunogenic emulsion compositions of the present invention are prepared using any of several methods well known in the art. Preferably, the emulsion compositions of the present invention are in the form of oil-in-water emulsions with submicron oil droplets, i.e., emulsions with dispersed (oil) phase droplets less than about 1 micron in diameter and in the nanometer size range. In order to produce such emulsions, a number of techniques can be used. For example, commercial emulsifiers can be used, which operate by the principle of high shear forces developed by forcing fluids through small apertures under high pressure. Examples of commercial emulsifiers include, without limitation, Model 110Y microfluidizer (Microfluidics, Newton, Mass.), Gaulin Model 30CD (Gaulin, Inc., Everett, Mass.), and Rainnie Minilab Type 8.30H (Miro Atomizer Food and Dairy, Inc., Hudson, Wis.). The appropriate pressure for use with an individual emulsion is readily determined by one of skill in the art. Further information regarding metabolizable oil emulsions can be found, for example, in commonly owned International Publication No. WO 00/50006 and in U.S. Pat. No. 6,299,884.

The size of the oil droplets can be varied, for example, by changing the ratio of emulsifying agent to oil (increasing the ratio typically decreases droplet size), operating pressure (increasing operating pressure typically decreases droplet size) and operating temperature (increasing temperature typically decreases droplet size). Droplet size will also vary with the particular emulsifying agent and oil used, as well as other components present, if any, at the time of emulsification (e.g., phospholipid, antigen, and optional supplemental compounds discussed below).

Droplet size can be verified by use of sizing instruments, such as the commercial Sub-Micron Particle Analyzer (Model N4MD) manufactured by the Coulter Corporation, and the method parameters can be varied, for example, using the guidelines set forth above until substantially all droplets are less than 1 micron in diameter, typically less than 0.8 microns in diameter, and more typically less than 0.5 microns in diameter. By "substantially all" is meant at least about 80% (by number), typically at least about 90%, more typically at least about 95% or even at least 98%. The particle size distribution is typically Gaussian, so that the average diameter is smaller than the stated limits.

According to one specific example, phospholipid, metabolizable oil, emulsifier having an HLB value ranging from 1-9 and, optionally, organic solvent are combined to provide an oil phase. Concurrently, emulsifier having an HLB value ranging from 10-18 is combined with water or another aqueous solution to provide an aqueous phase. The oil and aqueous phases are combined and subjected to a high-shear apparatus to create an emulsion containing dispersed (oil phase) particles of the desired size. The process is preferably completed by the removal of any residual organic solvent.

The antigen of interest can be provided within the immunogenic emulsion compositions of the present invention by a number of techniques. Typically, an emulsion is prepared from water, metabolizable oil, emulsifying agent and, optionally, phospholipid, as described above prior to adding the antigen that will be used in the vaccine. As noted, it may be desirable to initially prepare the emulsion using, for example, unadulterated water (e.g., deionized water), followed by the addition of the antigen within an appropriate buffer solution, to provide the final composition with the desired osmolality and pH. Since the emulsion compositions are typically stable, the antigen and emulsion can mixed by simple shaking. Other techniques, such as passing the antigen and emulsion rapidly through a small opening (such as a hypodermic needle), can readily provide a useful vaccine composition. However, it is not necessarily essential that the antigen of interest be added after formation of the emulsion composition. Instead, the antigen can be added prior to emulsification as discussed above.

Various components, such as the phospholipid and/or the optional supplemental components described below, can be introduced into the emulsion compositions of the present invention, for example, (a) if in oil-soluble or oil-dispersible form, by adding the additional component to the oil phase(s) or (b) if in water-soluble or water-dispersible form, by adding the additional component to the aqueous phase, either before or after emulsification.

4. Immunogenic Microparticle Compositions

Useful biodegradable polymers for forming the immunogenic microparticle compositions described herein include homopolymers, copolymers and polymer blends derived from the following: polyhydroxybutyric acid (also known as polyhydroxybutyrate); polyhydroxy valeric acid (also known as polyhydroxyvalerate); polyglycolic acid (PGA) (also known as polyglycolide); polylactic acid (PLA) (also known as polylactide); polydioxanone; polycaprolactone; polyorthoester; and polyanhydride. More typical are poly($\alpha$-hydroxy acids), such as poly(L-lactide), poly(D,L-lactide) (both known as APLA" herein), poly(hydroxybutyrates), copolymers of lactide and glycolide, such as poly(D,L-lactide-co-glycolides) (designated as "PLG" herein) or copolymers of D,L-lactide and caprolactone.

The above polymers are available in a variety of molecular weights, and the appropriate molecular weight for a given use is readily determined by one of skill in the art. Thus, for example, a suitable molecular weight for PLA may be on the order of about 2000 to 5000. A suitable molecular weight for PLG may range from about 10,000 to about 200,000, typically about 15,000 to about 150,000.

Where copolymers are used, copolymers with a variety of monomer ratios may be available. For example, where PLG is used to form the microparticles, a variety of lactide:glycolide molar ratios will find use herein, and the ratio is largely a matter of choice, depending in part on any coadministered adsorbed and/or entrapped species and the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. Mixtures of microparticles with varying lactide:glycolide ratios may also find use herein in order to achieve the desired release kinetics. Degradation rate of the microparticles of the present invention can also be controlled by such factors as polymer molecular weight and polymer crystallinity.

PLG copolymers with varying lactide:glycolide ratios and molecular weights are readily available commercially from a number of sources including from Boehringer Ingelheim, Germany and Birmingham Polymers, Inc., Birmingham, Ala. Some exemplary PLG copolymers include: (a) RG 502, a PLG having a 50:50 lactide/glycolide molar ratio and a molecular weight of 12,000 Da; (b) RG 503, a PLG having a 50:50 lactide/glycolide molar ratio and a molecular weight of 34,000 Da; (c) RG 504, a PLG having a 50:50 lactide/glycolide molar ratio and a molecular weight of 48,000 Da, (d) RG 752, a PLG having a 75:25 lactide/glycolide molar ratio and a molecular weight of 22,000 Da; and (e) RG 755, a PLG having a 75:25 lactide/glycolide molar ratio and a molecular weight of 68,000 Da. PLG polymers can also be synthesized by simple polycondensation of the lactic acid component using techniques well known in the art, such as described in Tabata et al., *J. Biomed. Mater. Res.* (1988) 22:837-858.

Where used, poly(D,L-lactide-co-glycolide) polymers are typically those having a molar lactide/glycolide molar ratio ranging from 20:80 to 80:20, more typically 40:60 to 60:40, and having a molecular weight ranging from 10,000 to 100,000 Daltons, more typically from 20,000 Daltons to 70,000 Daltons.

Microparticles are prepared using any of several methods well known in the art. For example, in some embodiments, double emulsion/solvent evaporation techniques, such as those described in U.S. Pat. No. 3,523,907 and Ogawa et al., *Chem. Pharm. Bull.* (1988) 36:1095-1103, can be used herein to make the microparticles. These techniques involve the formation of a primary emulsion consisting of droplets of polymer solution, which is subsequently mixed with a continuous aqueous phase containing a particle stabilizer/surfactant.

In other embodiments, microparticles can also be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) The "Wurster Process" in *Controlled Release Tech-* nologies: *Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst.* (1988) S(2):99-139; and ionic gelation as described by, e.g., Lim et al., *Science* (1980) 210:908-910.

In preferred embodiments, a water-in-oil-in-water (w/o/w) solvent evaporation system can be used to form the microparticles, along the lines described by O'Hagan et al., *Vaccine* (1993) 11:965-969, PCT/US99/17308 (WO 00/06123) to O'Hagan et al. and Jeffery et al., Pharm. Res. (1993) 10:362.

In general, a polymer of interest such as PLG is dissolved in an organic solvent, such as ethyl acetate, dimethylchloride (also called methylene chloride and dichloromethane), acetonitrile, acetone, chloroform, and the like. The polymer will typically be provided in about a 1-30%, more typically about a 2-15%, even more typically about a 3-10% and most typically, about a 4-8% solution, in organic solvent. The polymer solution is then combined with a first volume of aqueous solution and emulsified to form an o/w emulsion. The aqueous solution can be, for example, deionized water, normal saline, a buffered solution, for example, phosphate-buffered saline (PBS) or a sodium citrate/ethylenediaminetetraacetic acid (sodium citrate/ETDA) buffer solution. The latter solutions can (a) provide a tonicity, i.e., osmolality, that is essentially the same as normal physiological fluids and (b) maintain a pH compatible with normal physiological conditions. Alternatively, the tonicity and/or pH characteristics of the compositions of the present invention can be adjusted after microparticle formation and prior to administration. Preferably, the volume ratio of polymer solution to aqueous solution ranges from about 5:1 to about 20:1, more preferably about 10:1. Emulsification is conducted using any equipment appropriate for this task, and is typically a high-shear device such as, e.g., a homogenizer.

In some embodiments, one or more additional components are entrapped within the microparticles. For example, antigen, phospholipid and/or the optional supplemental components described below can be introduced by adding the same (a) to the polymer solution, if in oil-soluble or oil-dispersible form or (b) to the aqueous solution, if in water-soluble or water-dispersible form.

A volume of the o/w emulsion is then combined with a larger second volume of an aqueous solution, which typically contains a surfactant. The volume ratio of aqueous solution to o/w emulsion typically ranges from about 2:1 to 10:1, more typically about 4:1. Examples of surfactants appropriate for the practice of the invention are listed above. Those of ordinary skill in the art may readily select surfactants appropriate for the type of species to be adsorbed. For example, microparticles manufactured in the presence of charged surfactants, such as anionic or cationic surfactants, may yield microparticles with a surface having a net negative or a net positive charge, which can adsorb a wide variety of molecules. For example, microparticles manufactured with anionic surfactants, such as sodium dodecyl sulfate (SDS), e.g., SDS-PLG microparticles, adsorb positively charged species, for example, polypeptide-containing species such as proteins. Similarly, microparticles manufactured with cationic surfactants, such as CTAB, e.g., PLG/CTAB microparticles, adsorb negatively charged species, for example, polynucleotide-containing species such as DNA. Where the species to be adsorbed have regions of positive and negative charge, either cationic or anionic or nonionic surfactants may be appropriate. Certain species may adsorb more readily to microparticles having a combination of surfactants. Moreover, in some instances, it may be desirable to add surfactant to the above organic solution.

Where a cationic surfactant such as CTAB is used, it is typically provided in about a 0.00025-1% solution, more typically about a 0.0025-0.1% solution. Where an anionic surfactant such as DSS is used, it is typically provided in about a 0.00001-0.025% solution, more typically about a 0.0001-0.0025% solution. Where a nonionic surfactant such as PVA is used, it is typically provided in about a 2-15% solution, more typically about a 4-10% solution. For a cationic surfactant, a weight-to-weight surfactant-to-polymer ratio in the range of from about 0.00001:1 to about 0.5:1 is typically used; more typically from about 0.001:1 to about 0.1:1, and even more typically from about 0.0025:1 to about 0.05:1; for an anionic surfactant such as DSS, a weight-to-weight surfactant-to-polymer ratio in the range of from about 0.00001:1 to about 0.025:1 is typically used, more typically from about 0.0001:1 to about 0.0025:1; for a nonionic surfactant such as PVA a weight-to-weight surfactant-to-polymer ratio in the range of from about 0.001:1 to about 0.1:1 is typically used, more typically from about 0.0025:1 to about 0.05:1 is used.

This mixture is then homogenized to produce a stable w/o/w double emulsion. Each of the above homogenization steps is typically conducted at a room temperature (i.e., 25° C.) or less, more typically less, for example, while cooling within an ice bath.

Organic solvents are then evaporated. Following preparation, microparticles can be used as is or lyophilized for future use.

The formulation parameters can be manipulated to allow the preparation of small microparticles on the order of 0.05 μm (50 nm) to larger microparticles 50 μm or even larger. See, e.g., Jeffery et al., *Pharm. Res.* (1993) 10:362-368; McGee et al., *J. Microencap.* (1996). For example, reduced agitation typically results in larger microparticles, as do an increase in internal phase volume and an increase in polymer concentration. Small particles are typically produced by increased agitation as well as low aqueous phase volumes, high concentrations of emulsion stabilizers and a decrease in polymer concentration.

Particle size can be determined by, e.g., laser light scattering, using for example, a spectrometer incorporating a helium-neon laser. Generally, particle size is determined at room temperature and involves multiple analyses of the sample in question (e.g., 5-10 times) to yield an average value for the particle diameter. Particle size is also readily determined using scanning electron microscopy (SEM).

Upon preparation, a variety of components can be admixed with the microparticles, including antigen, phospholipid, and optional supplemental components such as those described below, and the resulting formulation can be lyophilized prior to use if desired. Typically, these components are added to the microparticles as an aqueous solution or dispersion. In some instances, these species will become adsorbed to the surface of the microparticles (see, e.g., the Examples below in which polypeptide antigens are adsorbed to the microparticle surface). The content of the adsorbed species can be determined using standard techniques.

Thus, the polymer microparticles of the present invention may have a variety of components entrapped or encapsulated within them, as well as having a variety of components adsorbed thereon. For example, one of ordinary skill in the art may prepare in accordance with the invention microparticles having adsorbed components, in addition to adsorbed antigen. One of ordinary skill in the art may also prepare in accordance with the invention microparticles having encapsulated components, such as antigen, phospholipid and/or any of the supplemental components described below.

5. Supplemental Components

The immunogenic compositions of the present invention can include a wide variety of optional supplemental components. Such supplemental components include: (a) pharmaceuticals such as antibiotics and antiviral agents, nonsteroidal antiinflammatory drugs, analgesics, vasodilators, cardiovascular drugs, psychotropics, neuroleptics, antidepressants, antiparkinson drugs, beta blockers, calcium channel blockers, bradykinin inhibitors, ACE-inhibitors, vasodilators, prolactin inhibitors, steroids, hormone antagonists, antihistamines, serotonin antagonists, heparin, chemotherapeutic agents, antineoplastics and growth factors, including but not limited to PDGF, EGF, KGF, IGF-1 and IGF-2, FGF, (b) hormones including peptide hormones such as insulin, proinsulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuromedins, neurotensin, pancreastatin, pancreatic polypeptide, substance P, secretin, thymosin, and the like, (c) enzymes, (d) transcription or translation mediators, (e) intermediates in metabolic pathways, (f) immunomodulators, such as any of the various cytokines including interleukin-1, interleukin-2, interleukin-3, interleukin-4, and gamma-interferon, and (g) supplementary immunological adjuvants such as those described below.

In the case of immunogenic microparticle compositions, such supplemental components can be, for example, adsorbed on the surface of the microparticles, entrapped within the microparticles, dissolved or dispersed in solution while unbound to the microparticles, adsorbed to or entrapped within another group of microparticles, and so forth.

In the case of immunogenic emulsion compositions, such supplemental components can be, for example, dissolved or dispersed within the oil phase(s) of the emulsion, dissolved or dispersed within the aqueous phase of the emulsion, disposed at the interface between the aqueous and oil phases of the emulsion, and so forth.

Supplementary immunological adjuvants may be used to enhance the effectiveness of the immunogenic compositions. For example, such immunological adjuvants may be administered concurrently with the immunogenic compositions of the present invention, e.g., in the same composition or in separate compositions. Alternatively, such adjuvants may be administered prior or subsequent to the immunogenic compositions of the present invention.

Supplementary immunological adjuvants include, but are not limited to: (1) aluminum salts (alum), such as aluminum hydroxide, aluminum phosphate, aluminum sulfate, etc.; (2) saponin adjuvants, such as Quil A, or QS21 (e.g., StimulonJ (Cambridge Bioscience, Worcester, Mass.)) may be used or particles generated therefrom such as ISCOMs (immunostimulating complexes), which ICOMS may be devoid of additional detergent e.g., WO00/07621; (3) Complete Freunds Adjuvant (CFA) and Incomplete Freunds Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) oligonucleotides comprising CpG motifs (Roman et al., *Nat. Med.*, 1997, 3, 849-854; Weiner et al., *PNAS USA*, 1997, 94, 10833-10837; Davis et al., *J. Immunol.* 1988, 160, 870-876; Chu et al., *J. Exp. Med.*, 1997, 186, 1623-1631; Lipford et al., *Eur. J. Immunol.* 1997, 27, 2340-2344; Moldoveanu et al., *Vaccine*, 1988, 16, 1216-1224, Krieg et al., *Nature*, 1995, 374, 546-549; Klinman et al., *PNAS USA*, 1996, 93, 2879-2883: Ballas et al., *J. Immunol.*, 1996, 157, 1840-1845; Cowdery et al., *J. Immunol.*, 1996, 156, 4570-4575; Halpern et al., *Cell. Immunol.*, 1996, 167, 72-78; Yamamoto et al., *Jpn. J. Cancer Res.*, 1988, 79, 866-873; Stacey et al., *J. Immunol*, 1996, 157, 2116-2122; Messina et al., *J. Immunol.*, 1991, 147, 1759-1764; Yi et al., *J. Immunol.*, 1996, 157, 4918-4925; Yi et al., *J. Immunol.*, 1996, 157, 5394-5402; Yi et al., *J. Immunol.*, 1998, 160, 4755-4761; and Yi et al., *J. Immunol.*, 1998, 160, 5898-5906; International patent applications WO96/02555, WO98/16247, WO98/18810, WO98/40100, WO98/55495, WO98/37919 and WO98/52581), i.e. oligonucleotides containing at least one CG dinucleotide (a cytosine nucleotide followed by a guanosine nucleotide), with 5 methylcytosine optionally being used in place of cytosine; (6) a polyoxyethylene ether or a polyoxyethylene ester e.g. WO99/52549; (7) a polyoxyethylene sorbitan ester surfactant in combination with an octoxynol (WO01/21207) or a polyoxyethylene alkyl ether or ester surfactant in combination with at least one additional nonionic surfactant such as an octoxynol (WO01/21152); (8) a saponin and an immunostimulatory oligonucleotide (e.g., a CpG oligonucleotide) (WO00/62800); (9) an immunostimulant and a particle of metal salt e.g. WO00/23105; (10) a saponin and an oil-in-water emulsion, e.g., WO99/11241; (11) a saponin (e.g. QS21)+3dMPL+IL-12 (optionally+a sterol), e.g., WO98/57659; (12) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63), LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); (13) adjuvants comprising natural or synthetic double-stranded RNA ("dsRNA"), which is generally made up of intermittent riboguanylic acid-ribocytidylic acid ([rG-rC]) and riboadenylic acid-polribouridylic acid ([rA-rU]) base pairs; for further information see, e.g., commonly owned PCT/US02/30423.; and (14) other substances that act as immunostimulating agents to enhance the effectiveness of the composition.

Muramyl peptides include, but are not limited to, N-acetyl-muramyl-L-threonyl-D-isoglutamine (thr-MDP), N-acetyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

For additional examples of adjuvants, see *Vaccine Design, The Subunit and the Adjuvant Approach*, Powell, M. F. and Newman, M. J, eds., Plenum Press, 1995).

6. Administration

Once formulated, the compositions of the invention can be administered parenterally, e.g., by injection (which may be needleless). The compositions can be injected subcutaneously, intraperitoneally, intravenously, intraarterially, intradermally, or intramuscularly, for example. Other modes of administration include nasal, mucosal, intraoccular, rectal, vaginal, oral and pulmonary administration, suppositories, and transdermal or transcutaneous applications.

In some embodiments, the compositions of the present invention can be used for site-specific targeted delivery. For example, intravenous administration of the compositions can be used for targeting the lung, liver, spleen, blood circulation, or bone marrow.

As can be seen from the above, the compositions of the present invention will generally include one or more pharmaceutically acceptable excipients. For example, vehicles such as water, saline, glycerol, polyethylene glycol, hyaluronic acid, ethanol, etc. may be used. Other excipients, such as wetting or emulsifying agents, biological buffering substances, and the like, may be present. A biological buffer can be virtually any solution which is pharmacologically acceptable and which provides the formulation with the desired pH, i.e., a pH in the physiological range. Examples include saline, phosphate buffered saline, Tris buffered saline, Hank's buffered saline, and the like. Depending on the final dosage form, other excipients known in the art can also be introduced, including binders, disintegrants, fillers (diluents), lubricants, glidants (flow enhancers), compression aids, colors, sweeteners, preservatives, suspending/dispersing agents, film formers/coatings, flavors and printing inks.

Treatment may be conducted according to a single dose schedule or a multiple dose schedule. A multiple dose schedule is one in which a primary course of administration may be given, for example, with 1-10 separate doses, followed by other doses given at subsequent time intervals, chosen to maintain and/or reinforce the therapeutic response, for example at 1-4 months for a second dose, and if needed, a subsequent dose(s) after several months. The dosage regimen will also be, at least in part, determined by the need of the subject and be dependent on the judgment of the practitioner.

Furthermore, if prevention of disease is desired, the compositions are generally administered prior to the arrival of the primary occurrence of the infection or disorder of interest. If other forms of treatment are desired, e.g., the reduction or elimination of symptoms or recurrences, the compositions are generally administered subsequent to the arrival of the primary occurrence of the infection or disorder of interest.

C. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Preparation and Characterization of Blank PLG Microparticles

Microparticles were prepared using a 6% w/v solution of RG504 polymer (a PLG Polymer having a 50:50 lactide/glycolide molar ratio and a molecular weight of 42-45 kDaltons, available from Boehringer Ingelheim) in methylene chloride. 10 ml of this solution was homogenized with 2.5 ml PBS using a 10-mm probe of a homogenizer (Ultra-Turrax T25 IKA-Labortechnik, Germany) for three minutes at 15,000 rpm, thereby forming a water-in-oil emulsion. This emulsion was then added to 50 ml of distilled water containing 6 ug/ml dioctyl sodium sulfosuccinate (DSS)(available from Sigma, USA) and homogenized at very high speed using a homogenizer with a 20-mm probe (ES-15 Omni International, GA, USA) for 25 minutes in an ice bath. This resulted in water-in-oil-in-water emulsion, which was stirred at 1000 rpm for 12 h at room temperature, allowing the methylene chloride to evaporate. The resulting microparticles were freeze dried. The resulting microparticles contained 0.05% DSS wt/wt. The size distribution of the resulting microparticles was determined using a particle size analyzer (Master Sizer, Malvern Instruments, UK), and was found to be between 0.8 and 1.2 p.m.

Example 2

Preparation and Characterization of PLG Microparticles with Entrapped Eisai 57 or Eisai 53

Microparticles were prepared by homogenizing 10 ml of 6% w/v of solution of RG504 PLG polymer in methylene chloride to which has been added either (a) 3 mg of Eisai57 (ER-804057, Eisai Co., Ltd., Tokyo, JP) phospholipid in a chloroform suspension or (b) 3 mg Eisai 53 (ER-804053, Eisai Co., Ltd., Tokyo, JP) phospholipid in an ethanol suspension, with 2.5 ml PBS using a 10-mm probe (Ultra-Turrax T25 IKA-Labortechnik, Germany) for three minutes at 15,000 rpm thus forming water-in-oil emulsions. Each of these emulsions was then added to 50 ml of distilled water containing 6 ug/mlDSS and homogenized at very high speed using a homogenizer with a 20-mm probe (ES-15 Omni International, GA, USA) for 25 minutes in an ice bath. This resulted in water-in-oil-in-water emulsions, which were stirred at 1000 rpm for 12 h at room temperature, while the methylene chloride was allowed to evaporate. The resulting microparticles were freeze-dried. The resulting microparticles contained 0.05% DSS wt/wt. The size distribution of the resulting microparticles was determined using a particle size analyzer (Master Sizer, Malvern Instruments, UK) and was found to be between 0.8 and 1.2 μm.

Example 3

Preparation of Injectable Compositions 10 mg (i.e., 10 ml of a 10 mg/ml suspension) of the DSS particles from Example 1 were incubated overnight at room temperature with 1 mg of meningitis B antigen ("MenB") (see, e.g., PCT/IB02/03904; WO 01/52885; Vol. 287 *Science,* 1816 (2000)) in 1 ml of histidine buffer (10 mmol; pH 5.0). The suspension was lyophilized after the addition of excipient (mannitol:sucrose, 45:15 mg/ml).

These compositions were (a) after reconstitution in water for injection, injected intramuscularly into mice ("PLG/MenB"), (b) combined with 0.1 ml of a solution containing 1.0 mg/ml CpG oligonucleotide (available from Oligos Inc., USA) in T.E. buffer ("PLG/MenB+sol CPG") and injected, (c) combined with 0.1 ml of a solution containing 1.0 mg/ml ER-804053 in ethanol ("PLG/MenB+sol Eisai53") and injected, (d) combined with 0.1 ml of a solution containing 1.0 mg/ml ER-804057 in ethanol ("PLG/MenB+sol Eisai57") and injected, (e) combined with 10 mg of lyophilized DSS particles with entrapped ER-804053 from Example 2 ("PLG/MenB+PLG/Eisai53") and injected, or (0 combined with 10 mg of lyophilized DSS particles with entrapped ER-804057 from Example 2 ("PLG/MenB+PLG/Eisai57") and injected.

Also, 100 mg lyophilized DSS particles with entrapped phospholipid from Example 2 were incubated overnight at room temperature with 1.0 mg of meningitis B antigen in 1 ml histidine buffer (pH 5.0). Each of these compositions (referred to herein as "PLG/Eisai53/MenB" or "PLG/Eisai57/MenB") was directly injected intramuscularly into mice.

In each of the above cases, the mice are boosted at 21 days and 35 days.

Example 4

Preparation and Characterization of MF59 Emulsion

500 µl of chloroform were placed in a 50 ml beaker, and 100 µl Span® 85 (available from Sigma, USA) and 1 ml squalene (available from Sigma, USA) were added and mixed. 100 µl Tween® 80 (from Sigma, USA) was added to 18.8 ml D.I. water and mixed by stirring for 15 min. The Tween® solution was added to the oil mixture and homogenized with a 10 mm probe (Ultra-Turrax T25 IKA-Labortechnik, Germany), for 1 min. The emulsified mixture was passed through a micro fluidizer (model M1105 from Microfluidics) at 90 psi 5 times. The residual chloroform was allowed to evaporate for 30 min. Emulsions are analyzed for size by dynamic light scattering yielding a <200 nm size distribution.

Example 5

Preparation and Characterization of Eisai57 and Eisai53 MF59 Emulsions

Oil-in-water emulsions were prepared with Eisa±57 or Eisai53 incorporated into the oil phase. Briefly, 800 µl of 5 mg/ml Eisai57 in chloroform and 800 µl of 5 mg/ml Eisai53 in chloroform were placed in separate 50 ml beakers. The chloroform was allowed to evaporate down to a volume of about 500 µl in each. 100 µl Span® 85 and 1 ml squalene were added to each and mixed. 100 µl Tween® 80 was added to 18.8 ml D.I. water and mixed by stirring for 15 min. The Tween® solution was added to each oil mixture and homogenized with a 10 mm probe (Ultra-Turrax T25 IKA-Labortechnik, Germany) for 1 min. Each emulsified mixture was passed through a micro fluidizer at 90 psi 5 times. Emulsions were analyzed for size by dynamic light scattering yielding a <200 nm size distribution.

Example 6

Preparation of Injectable Compositions

To 0.5 ml of each of the emulsions formed in Examples 4 and 5 was added 0.5 ml of a solution containing 0.2 mg/ml of antigen in PBS and the resulting compositions were mixed for 5 minutes. Antigens used were as follows: (a) meningitis B antigen, with the resulting injectable compositions referred to herein as "MF59+sol MenB", "MF59/Eisai53+sol MenB" and "MF59/Eisai57+sol MenB"; (b) HIV gp120 envelope protein (see, e.g., WO 00/06123; WO 02/26209), with the resulting injectable compositions referred to herein as "MF59+sol gp120", "MF59/Eisai53+sol gp120" and "MF59/Eisai57+sol gp120"; (c) HCV E1 E2 polypeptide (see, e.g., PCT/US02/20676), with the resulting injectable compositions referred to herein as "MF59+sol E1E2", "MF59/Eisai53+sol E1 E2" and "MF59/Eisai57+sol E1 E2".

To 0.5 ml of the emulsion formed in Example 4 was added (a) 0.5 ml of a solution containing 0.1 mg/ml of CpG oligonucleotide in PBS and (b) 0.5 ml of a solution containing 0.2 mg/ml of antigen in PBS. The resulting compositions were mixed for 5 minutes. Antigens used were as follows: (a) meningitis B protein ("MF59+sol MenB+sol CpG"); (b) HIV gp120 envelope protein ("MF59+sol gp120+sol CpG"); (c) HCV E1 E2 polypeptide ("MF59+sol E1 E2+sol CpG").

Each of these compositions was directly injected intramuscularly into mice. In each case, the mice are boosted at 21 days and 35 days.

Example 7

In Vivo Evaluation

Antibody Assays

Antigen-specific antibodies IgG and IgG isotypes (IgG1 and IgG2a) were determined by ELISA using 3,3,5,5'-tetramethylbenzidine-based colorimetric detection. ELISA plates (Nunc Maxisorb U96) were coated with 50 µl of the purified antigen at 5 µg/ml overnight at 4° C. The coated wells were blocked for 1 hr at 37° C. with 150 µl of 5% goat serum (Gibco BRL, Grand Island, N.Y.) in phosphate-buffered saline (PBS). The plates were washed three times with a washing buffer (PBS, 0.3% Tween-20), tapped, and dried. Serum samples and a serum standard were initially diluted in the blocking buffer and then transferred into coated, blocked plates in which the samples were serially diluted three-fold with the same buffer. Plates were washed after 1-hour incubation at 37° C. Horseradish peroxidase conjugated goat anti-mouse IgG gamma chain specific (Caltag Laboratories, Inc.) was used to determine the total IgG, and anti-mouse IgG1 and IgG2a were used to determine the isotypes. After the 1-hour incubation at 37° C., plates were washed to remove unbound antibodies. TMB substrate was used to develop the plates, and the color reaction was blocked after 15 minutes by the addition of 2N HCL. The titers of the antibodies were expressed as the reciprocal of the sample dilution, in which the optical density of the diluted sample equaled 0.5 at 450 nm. Results follow in Tables 2 and 3A-3C.

TABLE 2

GMT titers two weeks post $3^{rd}$ immunization.

| Formulation | Total IgG |
|---|---|
| PLG/MenB | 8245 |
| PLG/MenB + sol CPG | 14402 |
| PLG/MenB + sol Eisai53 | 43382 |
| PLG/MenB + sol Eisai57 | 72901 |
| PLG/MenB + PLG/Eisai53 | 35964 |
| PLG/MenB + PLG/Eisai57 | 34526 |
| PLG/Eisai53/MenB | 36310 |
| PLG/Eisai57/MenB | 44656 |

TABLE 3A

GMT titers three weeks post $3^{rd}$ immunization.

| Formulation | Total IgG | IgG2a | Ratio: (IgG2a)/ (MF59 + sol MenB) |
|---|---|---|---|
| MF59 + sol MenB | 46325 | 2530 | 1 |
| MF59 + sol MenB + sol CpG | 33985 | 5815 | 2.30 |
| MF59/Eisai53 + sol MenB | 98501 | 24508 | 9.69 |
| MF59/Eisai57 + sol MenB | 78366 | 19691 | 7.78 |

TABLE 3B

GMT titers three weeks post 3rd immunization.

| Formulation | Total IgG | IgG2a | Ratio: (IgG2a)/ (MF59 + sol gp120) |
|---|---|---|---|
| MF59 + sol gp120 | 764 | 25 | 1 |
| MF59 + sol gp120 + sol CpG | 5285 | 1753 | 70.12 |
| MF59/Eisai53 + sol gp120 | 5062 | 1941 | 77.64 |
| MF59/Eisai57 + sol gp120 | 13307 | 15618 | 624.7 |

TABLE 3C

GMT titers three weeks post 3rd immunization.

| Formulation | Total IgG | IgG2a | Ratio: (IgG2a)/ (MF59 + sol E1E2) |
|---|---|---|---|
| MF59 + sol E1E2 | 1090 | 2 | 1 |
| MF59 + sol E1E2 + sol CpG | 201 | 69 | 34 |
| MF59/Eisai53 + sol E1E2 | 774 | 256 | 128 |
| MF59/Eisai57 + sol E1E2 | 1205 | 562 | 281 |

Although preferred embodiments of the subject invention have been described in some detail, it is understood that obvious variations can be made without departing from the spirit and the scope of the invention.

The invention claimed is:

1. An immunogenic composition comprising: (a) water; (b) a metabolizable oil; (c) an emulsifying agent; (d) an antigen; and (e) a phospholipid compound comprising: (i) one or more

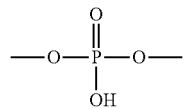

groups; (ii) 3 to 10 linear alkane groups,

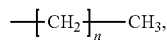

in which n is independently an integer ranging from 6 to 20, or a pharmaceutically acceptable salt thereof,
    wherein the composition is an oil-in-water emulsion having oil and aqueous phases, and
    wherein the oil phase is in the form of oil droplets substantially all of which are less than 1 micron in diameter.

2. The immunogenic composition of claim 1, wherein the phospholipid compound comprises

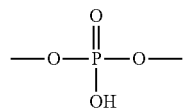

groups.

3. The immunogenic composition of claim 1, wherein the phospholipid compound comprises four to eight of said

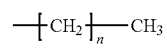

groups.

4. The immunogenic composition of claim 1, wherein the phospholipid compound comprises six of said

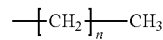

groups.

5. The immunogenic composition of claim 1, wherein the phospholipid compound does not comprise a saccharide group.

6. The immunogenic composition of claim 1, wherein the phospholipid compound is a compound having the following formula:

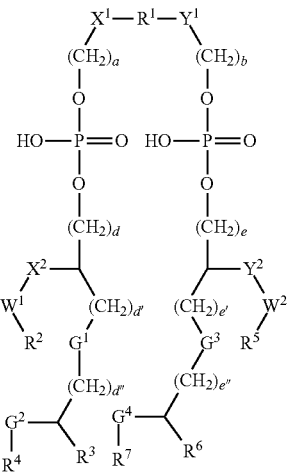

wherein:
$R^1$ is selected from the group consisting of
  (a) C(O);
  (b) C(O)—$C_{1-14}$ alkyl-C(O), wherein the $C_{1-14}$ alkyl is optionally substituted with hydroxy, $C_{1-5}$ alkoxy, $C_{1-5}$ alkylenedioxy, $C_{1-5}$ alkylamino, or $C_{1-5}$-alkyl-aryl, wherein the aryl moiety of the $C_{1-5}$-alkyl-aryl is optionally substituted with $C_{1-5}$ alkoxy, $C_{1-5}$ alkylamino, $C_{1-5}$ alkoxy-amino, $C_{1-5}$ alkylamino-$C_{1-5}$ alkoxy, —O—$C_{1-5}$ alkylamino-$C_{1-5}$ alkoxy, —O—$C_{1-5}$ alkylamino-C(O)—$C_{1-5}$ alkyl C(O)OH, —O—$C_{1-5}$ alkylamino-C(O)—$C_{1-5}$ alkyl-C(O)—$C_{1-5}$ alkyl;
  (c) $C_2$ to $C_{15}$ straight or branched chain alkyl optionally substituted with hydroxyl or alkoxy; and
  (d) —C(O)—$C_{6-12}$ arylene-C(O)— wherein the arylene is optionally substituted with hydroxy, halogen, nitro or amino;
a and b are independently 0, 1, 2, 3 or 4;
d, d', d", e, e' and e" are independently an integer from 1 to 4;
$X^1$, $X^2$, $Y^1$ and $Y^2$ are independently selected from the group consisting of a null, oxygen, NH and N(C(O)$C_{1-4}$ alkyl), and N($C_{1-4}$ alkyl)$_2$;
$W^1$ and $W^2$ are independently selected from the group consisting of carbonyl, methylene, sulfone and sulfoxide;
$R^2$ and $R^5$ are independently selected from the group consisting of:
  (a) $C_2$ to $C_{20}$ straight chain or branched chain alkyl which is optionally substituted with oxo, hydroxy or alkoxy, (b) $C_2$ to $C_{20}$ straight chain or branched chain alkenyl or dialkenyl which is Optionally substituted with oxo, hydroxy or alkoxy;

(c) $C_2$ to $C_{20}$ straight chain or branched chain alkoxy which is optionally substituted with oxo, hydroxy or alkoxy;

(d) —NH—$C_2$ to $C_{20}$ straight chain or branched chain alkyl, wherein the alkyl group is optionally substituted with oxo, hydroxy or alkoxy; and (e)

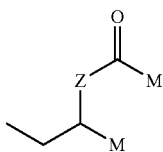

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;

$R^3$ and $R^6$ are independently selected from the group consisting of $C_2$ to $C_{20}$ straight chain or branched chain alkyl or alkenyl, optionally substituted with fluoro or oxo;

$R^4$ and $R^7$ are independently selected from the group consisting of $C(O)C_2$ to $C_{20}$ straight chain or branched chain alkyl or alkenyl; $C_2$ to $C_{20}$ straight chain or branched chain alkyl; $C_2$ to $C_{20}$ straight chain or branched chain alkoxy; $C_2$ to $C_{20}$ straight chain or branched chain alkenyl; wherein the alkyl, alkenyl or alkoxy groups are independently and optionally substituted with hydroxy, fluoro or $C_1$ to $C_5$ alkoxy;

$G^1$, $G^2$, $G^3$ and $G^4$ are independently selected from the group consisting of oxygen, methylene, amino, thiol, —NHC(O)—, and —N(C(O)$C_{1-4}$alkyl)-; or $G^2R^4$ or $G^4R^7$ may together be a hydrogen atom or hydroxyl;

or a pharmaceutically acceptable salt thereof.

7. The immunogenic composition of claim 6, wherein R1 is C(O); a, b, d, d', d", e, e' and e" are independently 1 or 2; X1, X2, Y1 and Y2 are NH; W1 and W2 are carbonyl; R2 and R5 are C10 to C20 straight chain alkyl which is substituted with oxo; R3 and R6 are C5-C10 straight chain alkyl; R4 and R7 are C(O)C8-C14 straight chain alkyl or alkenyl; and G1, G2, G3 and G4 are oxygen.

8. The immunogenic composition of claim 6, wherein R1 is C(O); a and b are 2; d, d', e and e' are 1; d" and e" are 2; X1, X2, Y1 and Y2 are NH; W1 and W2 are carbonyl; R2 and R5 are C13 straight chain alkyl which is substituted with oxo at the 2 position; R3 and R6 are C7 straight chain alkyl; R4 and R7 are C(O)C11 straight chain alkyl; G1, G2, G3 and G4 are oxygen.

9. The immunogenic composition of claim 1, wherein substantially all of the oil droplets are less than 500 nm in diameter.

10. The immunogenic composition of claim 1, wherein substantially all of the oil droplets are less than 250 nm in diameter.

11. The immunogenic composition of claim 1, wherein the metabolizable oil is selected from an animal oil and a vegetable oil.

12. The immunogenic composition of claim 1, wherein the metabolizable oil is a Fish oil.

13. The immunogenic composition of claim 1, wherein the metabolizable oil is a branched, polyunsaturated hydrocarbon having from 20-40 carbon atoms.

14. The immunogenic composition of claim 1, wherein the metabolizable oil is a terpenoid.

15. The immunogenic composition of claim 1, wherein the metabolizable oil is squalene.

16. The immunogenic composition of claim 1, wherein the emulsifying agent comprises a sorbitan derivative.

17. The immunogenic composition of claim 16, wherein the sorbitan derivative is selected sorbitan fatty acid monoesters, sorbitan fatty acid sesquiesters, sorbitan fatty acid triesters, polyoxyethylene sorbitan fatty acid monoesters and polyoxyethylene sorbitan fatty acid triesters.

18. The immunogenic composition of claim 1, wherein the composition comprises a plurality of emulsifying agents.

19. The immunogenic composition of claim 18, wherein the composition comprises a sorbitan ester and a polyoxyethylene sorbitan ester.

20. The immunogenic composition of claim 19, wherein the composition comprises polyoxyethylene sorbitan monooleate and sorbitan trioleate.

21. The immunogenic composition of claim 18, wherein the composition comprises a first emulsifying agent having an HLB value ranging from 1 to 9 and a second emulsifying agent having an HLB value ranging from 10 to 20.

22. The immunogenic composition of claim 18, wherein the composition comprises a first emulsifying agent having an HLB value ranging from 1 to 4 and a second emulsifying agent having an HLB value ranging from 12 to 17.

23. The immunogenic composition of claim 1, wherein the phospholipid is dissolved or dispersed in the oil phase.

24. The immunogenic composition of claim 1, wherein the phospholipid is dispersed in the aqueous phase.

25. The immunogenic composition of claim 1, wherein the antigen is dissolved or dispersed in the aqueous phase.

26. The immunogenic composition of claim 1, wherein the antigen is a polypeptide-containing antigen.

27. The immunogenic composition of claim 1, wherein the antigen is a polynucleotide-containing antigen.

28. The immunogenic composition of claim 1, wherein the antigen is derived from a tumor cell.

29. The immunogenic composition of claim 1, wherein the antigen is derived from a pathogenic organism.

30. The immunogenic composition of claim 29, wherein the pathogenic organism is selected from a virus, a bacterium, a fungus and a parasite.

31. The immunogenic composition of claim 29, wherein the pathogenic organism is selected from HIV, hepatitis B virus, hepatitis C virus, meningitis B, *Haemophilus influenza* type B, pertussis, diphtheria, tetanus, and influenza A virus.

32. The immunogenic composition of claim 29, wherein the pathogenic organism is selected from human immunodeficiency virus, *Neisseria meningitidis*, and hepatitis virus.

33. The immunogenic composition of claim 1, further comprising a supplemental immunological adjuvant.

34. The immunogenic composition of claim 1, wherein the immunogenic composition is an injectable composition.

35. A method of delivering a therapeutic amount of an antigen to a vertebrate host animal, comprising administering to the host animal the immunogenic composition of claim 1.

36. A method of treating a host animal having a pathogenic organism infection or tumor comprising administering to the animal the immunogenic composition of claim 1.

37. A method of immunizing a host animal against a tumor or infection by a pathogenic organism comprising administering to the animal the immunogenic composition of claim 1.

38. A method of stimulating an immune response in a host animal, comprising administering to the host animal the immunogenic composition of claim 1.

39. The method of claim 38, wherein the immune response comprises a humoral immune response.

40. The method of claim 38, wherein the immune response comprises a cellular immune response.

41. The method of claim 38, wherein the immune response is raised against a viral, bacterial, or parasitic infection.

42. The method of claim 38, wherein the immune response is raised against a tumor.

43. The method of claim 38, wherein the host animal is a vertebrate animal.

44. The method of claim 38, wherein the host animal is a mammal.

45. The method of claim 38, wherein the host animal is a human.

\* \* \* \* \*